(12) United States Patent
Moradi et al.

(10) Patent No.: US 10,781,176 B2
(45) Date of Patent: Sep. 22, 2020

(54) CATALYTIC HYDROGENATION OF SUBSTITUTED CYANOPYRIDINES AND PROCESS FOR PREPARING SUBSTITUTED PYRIDYLMETHYLBENZAMIDES

(71) Applicant: BAYER CROPSCIENCE AKTIENGESELLSCHAFT, Moheim am Rhein (DE)

(72) Inventors: Wahed Ahmed Moradi, Monheim (DE); Günter Schlegel, Leverkusen (DE); Albert Schnatterer, Leverkusen (DE); Frank Volz, Köln (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/569,528

(22) PCT Filed: Apr. 26, 2016

(86) PCT No.: PCT/EP2016/059215
§ 371 (c)(1),
(2) Date: Oct. 26, 2017

(87) PCT Pub. No.: WO2016/173998
PCT Pub. Date: Nov. 3, 2016

(65) Prior Publication Data
US 2018/0297952 A1 Oct. 18, 2018

(30) Foreign Application Priority Data
Apr. 30, 2015 (EP) .................................... 15165831

(51) Int. Cl.
*C07D 213/61* (2006.01)
*C07D 213/40* (2006.01)

(52) U.S. Cl.
CPC ......... *C07D 213/61* (2013.01); *C07D 213/40* (2013.01)

(58) Field of Classification Search
CPC .................................................. C07D 213/61
See application file for complete search history.

(56) References Cited

U.S. PATENT DOCUMENTS

| 5,105,011 A | 4/1992 | Cordier et al. | |
| 6,503,933 B1 * | 1/2003 | Moloney ............. | A01N 43/40 514/345 |
| 6,921,828 B2 * | 7/2005 | Dann .................... | C07D 213/26 546/286 |
| 7,700,593 B2 * | 4/2010 | Zhang ................. | C07D 471/04 514/233.2 |
| 2003/0171410 A1 | 9/2003 | Moloney et al. | |

FOREIGN PATENT DOCUMENTS

| AU | 3367793 A | 9/1993 | |
| CN | 1291187 A | 4/2001 | |
| EP | 0 409 716 A2 | 1/1991 | |
| EP | 1 199 305 A1 | 4/2002 | |
| EP | 1 422 221 A1 | 5/2004 | |
| JP | 07138209 A * | 5/1995 | |
| WO | 99/42447 A1 | 8/1999 | |
| WO | 02/16322 A2 | 2/2002 | |
| WO | WO-2013048928 A1 * | 4/2013 | ........... C07D 403/12 |

OTHER PUBLICATIONS

Wünsch "Catalytic Hydrogenation" Science of Synthesis, (2009) 40, 29-64.*
Blaser "1.2 Heterogeneous Hydrogenation: a Valuable Tool for the Synthetic Chemist" in Transition Metals for Organic Synthesis, vol. 2, 2nd Edition 2004 Wiley-VCH: Weinheim.*
Freifelder, Practical Catalytic Hydrogenation Techniques and Applications Wiley: New York 1971, 1-83, 238-260.*
Homer, "Versuche zum Vorgang der Wasserstoffübertragung, VI, Strukturelle Abhangigkeit Der Giftwirkung Organischer Substanzen Auf Raney-Nickel Als Hydrierungskatalysator" Justus Liebigs Annalen der Chemie, 1962, 660, 1-23.*
Evdokimova "Selectivity issues in the catalytic multiphase reduction of functionalized halogenated aromatics over Pd/C, Pt/C, and Raney-Ni" Applied Catalysis A: General 271 (2004) 129-136.*
International Search Report of PCT/EP2016/059215 dated Jul. 6, 2016.
John Wile "Hydrogenation of Nitriles", Handbook of 5 Heterogeneous Catalytic Hydrogenation for Organic Synthesis, pp. 254-285, New York 2001.

* cited by examiner

Primary Examiner — David K O'Dell
(74) Attorney, Agent, or Firm — McBee Moore & Vanik IP, LLC

(57) ABSTRACT

The present invention relates to novel processes for the preparation of substituted pyridyl-methylbenzamide derivatives of formula (I), in particular 2,6-dichloro-N-{[3-chloro-5-(trifluoromethyl)-2-pyridyl]methyl}benzamide (Fluopicolide), and for the catalytic hydrogenation of substituted cyanopyridine derivatives, in particular 3-chloro-2-cyano-5-trifluoromethylpyridine [=Py-CN] to the corresponding substituted 2-methylaminopyridine derivatives, in particular 2-aminomethyl-3-chloro-5-trifluoromethylpyridine [=Py-methylamine] or salts thereof in the presence of metal catalysts such as in particular palladium catalysts, catalytic modifiers and acids.

18 Claims, No Drawings

CATALYTIC HYDROGENATION OF SUBSTITUTED CYANOPYRIDINES AND PROCESS FOR PREPARING SUBSTITUTED PYRIDYLMETHYLBENZAMIDES

CROSS REFERENCE TO RELATED APPLICATIONS

This application is a § 371 National State Application of PCT/EP2016/059215, filed Apr. 26, 2016, which claims priority to European Application No. 15165831.7 filed Apr. 30, 2015.

BACKGROUND OF THE INVENTION

Field of the Invention

The present invention relates to novel processes for the preparation of substituted pyridylmethylbenzamide derivatives of formula (I), in particular 2,6-dichloro-N-{[3-chloro-5-(trifluoromethyl)-2-pyridyl]methyl}benzamide (Fluopicolide), and for the catalytic hydrogenation of substituted cyanopyridine derivatives, in particular 3-chloro-2-cyano-5-trifluoromethylpyridine [=Py-CN] to the corresponding substituted 2-methylaminopyridine derivatives, in particular 2-aminomethyl-3-chloro-5-trifluoromethylpyridine [=Py-methylamine] or salts thereof in the presence of metal catalysts such as in particular palladium catalysts, catalytic modifiers and acids.

Description of Related Art

Substituted pyridylmethylbenzamide derivatives of formula (I)

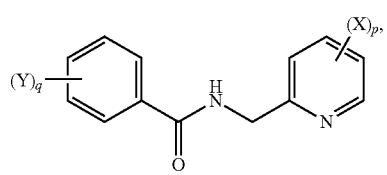

wherein
p is an integer equal to 1, 2, 3 or 4,
q is an integer equal to 1, 2, 3 or 4,
each substituent X is chosen, independently of the others, as being hydrogen, halogen, $C_1$-$C_4$ alkyl or $C_1$-$C_4$ haloalkyl with the proviso that at least one X is halogen,
Y is halogen,
are highly active against phytopathogenic fungi. Compounds of formula (I) are described in EP-B-1056723.

Substituted cyanopyridine derivatives, wherein the substitution is present on the pyridine ring, such as in particular 3-chloro-2-cyano-5-trifluoromethylpyridine are important intermediates for the preparation of Fluopicolide (2,6-dichloro-N-{[3-chloro-5-(trifluoromethyl)-2-pyridyl]methyl}benzamide), a commercially available fungicide, according to formula (Ia) shown below

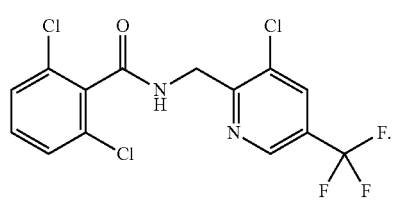

In general the catalytic hydrogenation of nitriles is well known in the literature and can be carried out with different catalysts under either acidic or basic condition (Nishimura in "Handbook of Heterogeneous Catalytic Hydrogenation for Organic Synthesis", pp. 254-285, John Wiley and Sons, New York, 2001). It is also known that the catalytic hydrogenation of nitriles to the desired primary amines is usually accompanied by the formation of significant amounts of secondary and tertiary amines which contaminate the desired primary amine and makes the isolation very complicated, costly and inefficient and thus not suitable for being used on an industrial scale.

The production of fluopicolide via catalytic hydrogenation is described in WO-A 2002/16322.

WO-A 2002/16322 discloses concretely the catalytic hydrogenation of 3-chloro-2-cyano-5-trifluoromethylpyridine [Py-CN] into 2-aminomethyl-3chloro-5-trifluoromethylpyridine [=Py-methylamine] in the presence of a palladium catalyst on charcoal in a protic solvent being methanol. The method described in WO-A 2002/16322 has the drawback in that the yield of the hydrogenation reaction from [Py-CN] to [Py-methylamine] is low. Another difficulty with this process is the potential for catalyst deactivation by the large amount of side products formed which could amount up to 5% of the end product. Side products include but are not limited to dechlorinated compounds, in particular of 2-[5-(trifluoromethyl)pyridin-2-yl]methanamine. In addition, the reaction mixture contains large amounts of hydrochloric acid and is therefore highly corrosive. The solvent methanol reacts with the hydrochloric acid forming the gas chloromethane which is toxic and needs to be separated. Consequently the process described is disadvantageous from the economic, environmental and safety standpoint.

The low selectivity to the desired product and the formation of different side products makes the economic isolation of the compound according to formula (III) not acceptable at an industrial scale.

The described prior art process(es) are therefore not suitable for a large scale production. In contrast, the new process of the present invention, as described in detail hereinafter, provides an economic process with significantly reduced formation of unwanted side-products, particularly with reduced formation of unwanted dehalogenated side-products, and remarkably increased yield of the desired reaction products.

The chemoselective catalytic hydrogenation of substituted cyanopyridines according to formula (II) as disclosed below wherein at least one of the X substituents is halogen is in general problematic. Such compounds are easily dehalogenated during the catalytic hydrogenation thus forming undesired dehalogenated side-products.

A respective of substituted cyanopyridine derivative according to formula (II), wherein at least one X substituent is halogen, preferably chlorine, can be defined by the following formula (II') below. Upon dehalogenation during the catalytic hydrogenation process, the corresponding dehalogenated compounds of formula (II"), as defined below, can be formed.

| Halogen substituted compound (preferably chlorine substituted compound) | corresponding dehalogenated compound (preferably dechlorinated compound) |
|---|---|
| <br>(II')<br>p = 1, 2, 3 or 4<br>each substituent X is chosen, independently of the others, as being hydrogen, halogen, $C_1$-$C_4$ alkyl or $C_1$-$C_4$ haloalkyl with the proviso that at least one substituent X is halogen, preferably chlorine | <br>(II'')<br>p = 1, 2, 3 or 4<br>each substituent X is chosen, independently of the others, as being hydrogen, halogen, $C_1$-$C_4$ alkyl or $C_1$-$C_4$ haloalkyl with the proviso that the at least one halogen substituent, preferably chlorine substituent, of the corresponding compound (II') is replaced by hydrogen |

SUMMARY

It is therefore an object of the present invention to provide a novel, safer, more economically and environmentally viable process suitable for industrial scale for preparing substituted 2-methylaminopyridine derivatives of the formula (III) from substituted cyanopyridyl derivatives of the formula (II), as defined below. The process described herein does in particular lead to less dehalogenated side-products.

The production of Fluopicolide (formula (Ia)) from compounds of formula (III) is known in the art e.g. from WO 99/42447 and WO-A 2002/16322. These documents describe the formation of substituted pyridylmethylbenzamide derivatives by acylation of 2-methylaminopyridine derivatives with substituted benzoyl derivatives. However the process described in WO 99/42447 and WO-A 2002/16322 to obtain substituted pyridylmethylbenzamide derivatives of formula (I), for example Fluopicolide of formula (Ia), bears several disadvantages such as low yield of the hydrogenation step, formation of dehalogenated side products, isolation of 2-methylaminopyridine derivatives of the formula (III) and stability issues with the isolated material. It is therefore a further object of the present invention to provide a novel, safer, more economically and environmentally viable process suitable for industrial scale for preparing substituted pyridylmethylbenzamide derivatives of the formula (I) from substituted 2-methylaminopyridine derivatives of the formula (III).

The object was achieved according to the present invention by a process (A1) for preparing substituted 2-methylaminopyridine derivatives of the formula (III) and corresponding salts thereof,

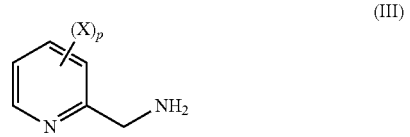

(III)

wherein p is an integer equal to 1, 2, 3 or 4;

each substituent X is chosen, independently of the others, as being halogen, $C_1$-$C_4$ alkyl or $C_1$-$C_4$ haloalkyl;

characterized in that in step (A) a substituted cyanopyridyl derivative according to formula (II)

(II)

wherein p is an integer equal to 1, 2, 3 or 4;

each substituent X is chosen, independently of the others, as being halogen, $C_1$-$C_4$ alkyl or $C_1$-$C_4$ haloalkyl;

is hydrogenated in the presence of a metal catalyst, a catalyst modifier, and an acid, wherein the amount of the catalyst modifier is in the range from about 0.0000001 equivalents to about 10 equivalents with respect to the amount of cyanopyridyl derivative according to formula (II).

DETAILED DESCRIPTION OF A PREFERRED EMBODIMENT

The production of Fluopicolide (formula Ia) from compounds of formula (III) is known to a skilled person in the art e.g. from WO-A 2002/16322.

Process (A) may comprise an additional step (A1a) after step (A1), wherein a suitable base is added to the reaction mixture comprising the 2-methylaminopyridine derivative of formula (III) after filtering off the catalyst to adjust the pH value.

Process (A) may comprise an additional step (A2) after step (A1) or (A1a), wherein the solvent of the reaction solution comprising the 2-methylaminopyridine derivative according to formula (III) is removed;

Process (A) may comprise an additional step (A3) after steps (A1) and (A2), wherein a base and optionally before, at the same time or thereafter an organic solvent is added to the remaining residue of step (A2);

Process (A) may comprise an additional step (A4) after steps (A1), (A2), and (A3), wherein the organic phase (non-water soluble) is separated from the water phase and wherein optionally an acid is added to the organic phase.

Process (A) may comprise an additional step (A5) after steps (A1), (A2), (A3) and (A4) wherein the precipitated product according to formula (III) is isolated from the reaction suspension comprising the 2-methylaminopyridine derivative according formula (III).

A further object of the present invention is a process (B) for the preparation of substituted pyridylmethylbenzamides of formula (I)

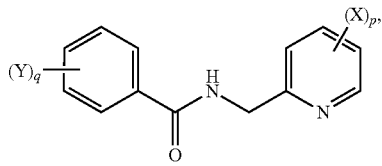

(I)

wherein p is an integer equal to 1, 2, 3 or 4, q is an integer equal to 1, 2, 3 or 4, each substituent X is chosen, independently of the others, as being hydrogen, halogen, $C_1$-$C_4$ alkyl or $C_1$-$C_4$ haloalkyl with the proviso that the at least one X is halogen, Y is halogen, characterized in that in a step (B2) a compound of formula (III) or corresponding salts thereof is reacted in a suitable solvent in the presence of a suitable base with a compound of formula (IV)

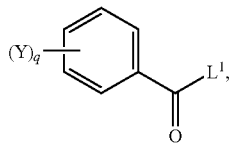

(IV)

wherein q is an integer equal to 1, 2, 3 or 4,

Y is halogen and $L^1$ is a leaving group.

A further object of the present invention is a process (B) for the preparation of substituted pyridylmethylbenzamides of formula (I)

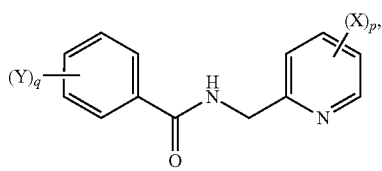

(I)

wherein p is an integer equal to 1, 2, 3 or 4, q is an integer equal to 1, 2, 3 or 4, each substituent X is chosen, independently of the others, as being hydrogen, halogen, $C_1$-$C_4$ alkyl or $C_1$-$C_4$ haloalkyl with the proviso that the at least one X is halogen, Y is halogen, characterized in that in a step (B1) a substituted cyanopyridyl derivative according to formula (II)

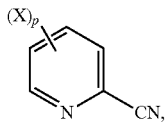

(II)

wherein p and X are defined as above, is hydrogenated in the presence of a metal catalyst, a catalyst modifier and an acid, wherein the amount of the catalyst modifier is in the range from about 0.0000001 equivalents to about 10 equivalents with respect to the amount of cyanopyridyl derivative according to formula (II), to give a compound of formula (III) or corresponding salts thereof

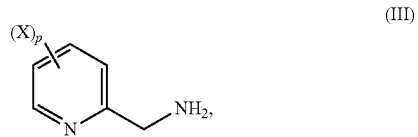

(III)

wherein p and X are defined as above, which is reacted in a step (B2) in a suitable solvent in the presence of a suitable base with a compound of formula (IV)

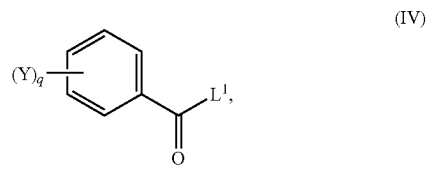

(IV)

wherein q is an integer equal to 1, 2, 3 or 4,

Y is halogen and $L^1$ is a leaving group.

Process (B) may comprise an additional step (B1a) after step (B1), wherein a suitable base is added to the reaction mixture comprising the 2-methylaminopyridine derivative of formula (III) after filtering off the catalyst to adjust the pH value.

Process (B) may comprise an additional step (B3) after step (B2), wherein a suitable acid is added to the reaction mixture comprising the pyridylmethylbenzamide derivative of formula (I) to adjust the pH.

Process (B) may comprise an additional step (B4) after step (B3), wherein the reaction mixtures comprising the pyridylmethylbenzamide derivative of formula (I) is filtered and the residue washed with a suitable solvent.

Unless otherwise stated, the following definitions apply for the substituents and residues used throughout this specification and claims:

In each case, X is preferably independently of the others, as being fluorine, chlorine, bromine, $C_1$-$C_2$ alkyl or $C_1$-$C_2$ haloalkyl having 1 to 5 halogen atoms selected independently from each other from fluorine, chlorine;

In each case, X is more preferably independently of the others, as being fluorine, chlorine, methyl, ethyl or $C_1$-$C_2$ haloalkyl having 1 to 5 halogen atoms selected independently from each other from fluorine, chlorine;

In each case, X is particular preferably independently of the others, as being fluorine, chlorine, or difluoromethyl, trifluoromethyl, dichloromethyl, trichloromethyl;

In each case, X is very particular preferably independently of the others, as being chlorine, or trifluoromethyl.

As regards the positions in which the 2-pyridyl moiety is substituted by X, the 2-pyridyl moiety is preferably substituted by X in 3- and/or in 5-position. Preferably, the 2-pyridyl moiety is substituted by X in 3- and 5-position.

Very particular preferably the compound according to formula (II) is 3-chloro-2-cyano-5-trifluoromethylpyridine [=Py-CN].

In each case, Y is preferably independently of the others, as being fluorine, chlorine, bromine.

In each case, Y is very preferably independently of the others, as being fluorine, chlorine.

In each case, Y is very particular preferably as being chlorine.

As regards the positions in which the benzoyl moiety is substituted by Y, the benzoyl moiety is preferably substituted by Y in 2- and/or in 6-position. Particular preferably, the benzoyl moiety is substituted by X in 2- and 6-position.

Very particular preferably the compound according to formula (IV) is 2,6-dichlorobenzoylchloride.

In each case, p is preferably an integer equal to 1, 2 or 3.

In each case, p is very preferably an integer equal to 1 or 2.

In each case, p is very particular preferably an integer equal to 2.

In each case, q is preferably an integer equal to 1, 2 or 3.

In each case, q is very preferably an integer equal to 1 or 2.

In each case, q is very particular preferably an integer equal to 2.

In each case leaving group $L^1$ is halogen, as being chlorine, bromine, iodine.

In each case leaving group $L^1$ is preferably chlorine.

Very particular preferably the compound according to formula (I) is Fluopicolide as defined in formula (Ia).

Particular preferably an object of the present invention is a process (B) for the preparation of a substituted pyridylmethylbenzamide of formula (Ia)

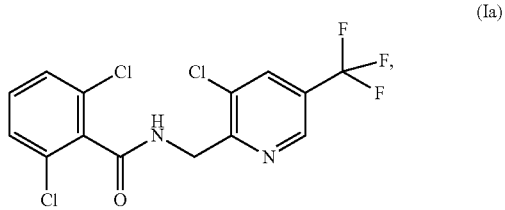 [SMILES: O=C(NCc1ncc(C(F)(F)F)cc1Cl)c1c(Cl)cccc1Cl]

(Ia)

characterized in that in a step (B2) a compound of formula (IIIa)

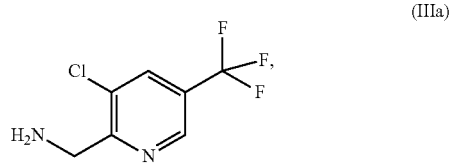 [SMILES: NCc1ncc(C(F)(F)F)cc1Cl]

(IIIa)

or corresponding salts thereof is reacted in a suitable solvent in the presence of a suitable base with a compound of formula (IVa)

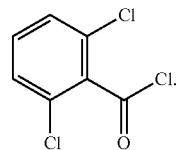

(IVa)

Particular preferably an object of the present invention is a process (B) for the preparation of substituted pyridylmethylbenzamides of formula (Ia)

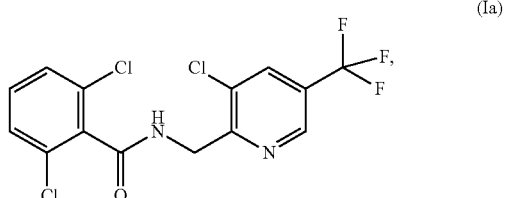

(Ia)

characterized in that in a step (B1) a substituted cyanopyridyl derivative according to formula (Ia)

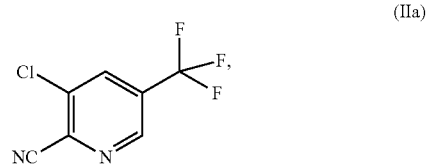 [SMILES: N#Cc1ncc(C(F)(F)F)cc1Cl]

(IIa)

is hydrogenated in the presence of a metal catalyst, a catalyst modifier and an acid, wherein the amount of the catalyst modifier is in the range from about 0.0000001 equivalents to about 10 equivalents with respect to the amount of cyanopyridyl derivative according to formula (IIa), to give a compound of formula (IIIa) or corresponding salts thereof

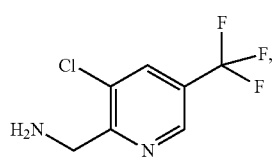

(IIIa)

which is reacted in a step (B2) in a suitable solvent in the presence of a suitable base with a compound of formula (IVa)

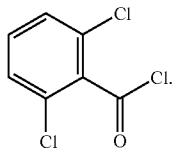

(IVa)

The corresponding salts of the compounds according to formula (I) are preferably hydrogensulfates, sulfates, hydrogensulfate-sulfate mixtures, hydrochlorides, phosphates, formates, or acetates. Particular preferably hydrogensulfates, sulfates or mixtures thereof.

Throughout the invention the term equivalent refers to molar equivalents.

Alkyl represents a straight-chain or branched saturated hydrocarbon radical having 1 to 4 carbon atoms. Non-limiting examples include methyl, ethyl, propyl, 1-methylethyl (iso-propyl), n-butyl, 1-methylpropyl (iso-butyl), 2-methylpropyl (sec-butyl), 1,1-dimethylethyl (tert.-butyl). Preference is given to $C_1$-$C_2$-alkyl representing a straight-chain saturated hydrocarbon radical having 1 or 2 carbon atoms, such as methyl or ethyl.

Haloalkyl represents in general an alkyl-radical having 1 to 4 carbon atoms, in which 1 up to all hydrogen atoms are replaced by halogen atoms. Non-limiting examples include chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl. Preference is given to difluoromethyl, trifluoromethyl, dichloromethyl, trichloromethyl.

Suitable bases for step (A1a) are inorganic bases such $Na_2CO_3$, $NaHCO_3$, $K_2CO_3$, $KHCO_3$, NaOH, KOH, Ca$(OH)_2$, $Mg(OH)_2$ or organic bases such as triethyl amine, N,N-diisopropylethylamine. Particularly preferred for step (A1a) are $Na_2CO_3$, $K_2CO_3$, NaOH, KOH and Ca$(OH)_2$. More preferred are NaOH, KOH, Ca$(OH)_2$. Mostly preferred are NaOH, KOH. Preferably, in step (A1a) a base as defined herein is added until adjustment of the pH value of the reaction solution to pH 4 to 14, particular preferably pH 6 to 9 is achieved.

Useful bases which may be used in the process according to the present invention, such as in particular in step (A3) are inorganic or organic bases such as $Na_2CO_3$, $NaHCO_3$, $K_2CO_3$, $KHCO_3$, NaOH, KOH, Ca$(OH)_2$, $Mg(OH)_2$, triethyl amine, N,N-diisopropylethylamine.

The following bases are particularly preferred for step (A3): $Na_2CO_3$, $NaHCO_3$, $K_2CO_3$, $KHCO_3$, NaOH, KOH, Ca$(OH)_2$. More preferred are NaOH, KOH, Ca$(OH)_2$. Mostly preferred are NaOH, KOH. Preferably, in step (A3) a base as defined herein is added until adjustment of the pH value of the reaction solution to pH 4 to 14, preferably pH 6 to 13 is achieved.

The metal catalyst is any hydrogenation catalyst selected from the group of palladium, platinum, ruthenium, and rhodium catalysts. In one embodiment the metal catalyst is any hydrogenation catalyst selected from the group of palladium, platinum, and ruthenium catalysts.

In one embodiment the metal catalyst is any hydrogenation catalyst selected from the group of palladium, platinum, and rhodium catalysts. Palladium (Pd), platinum (Pt) or a combination thereof as catalysts are preferred catalytically active metal catalysts. Palladium (Pd), platinum (Pt) or a combination thereof or Rhodium catalysts are preferred catalytically active metal catalysts. Particularly preferred are palladium catalysts. Even more preferred are palladium catalysts from the group consisting of elemental palladium and palladium compounds which are reducible by hydrogen or any other reducing agents (e.g. sodium formate, hydrazine) to elemental palladium at the hydrogenation conditions as applied in the process of the present invention, and mixtures thereof.

The metal catalysts may be present in any chemical form, for example in elemental, colloidal, salt or hydroxide, oxide form, together with complexing agents as chelates. The metal catalysts may be present in supported form, i.e. applied to any support, preferably an organic or inorganic support. Examples of suitable supports are carbon (charcoal or activated carbon), aluminium oxide, silicon dioxide, zirconium dioxide, titanium dioxide, calcium carbonate, barium sulphate and zeolite. Preferred supports are carbon such as charcoal and activated carbon.

The metal loading on such a support is between 0.01% and 100%, more preferably in the range of 0.5% to 50% and even more preferably in the range of 0.5% to 25%, and most preferably in the range of 1% to 20% and between 5% and 20%. Further preferred ranges further include a metal loading on such support between 0.5% and 10%, between 0.5% and 20%, between 1% and 10%, between 1% and 5%, between 1% and 3%, between 3% and 10%, between 3% and 20%, and between 5% and 10%.

Preferred catalysts in supported form are selected from palladium and platinum catalysts, with palladium catalysts in supported form being particularly preferred.

Therefrom, preferred catalysts, which are present in supported form, are Pd/C, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/CaCO$_3$, Pd/C-diphenylsulfide, Pd/Al$_2$O$_3$, Pd/SiO$_2$, Pd/BaSO$_4$, Pd(II)acetate-Polymethylhydrosiloxane, Pd (Fe)/C, Pd/C 5% sulfur, Pt/C, Pt/C-5% sulfur, Pt/Al$_2$O$_3$.

Further suitable catalysts are Pd/V catalysts such as 5% Pd/0.5% V, Pd/Pt catalysts such as 4% Pd/1% Pt.

Particularly preferred catalysts, which are present in supported form, are Pd/C, Pd/Al$_2$O$_3$, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/SiO$_2$.

Very particularly preferred catalysts are Pd/C, Pd/Al$_2$O$_3$, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/SiO$_2$ having a metal loading in the range of 0.5% to 25%, preferably in the range of 0.5% to 25%, more preferably in the range of 1% to 20%, even more preferably in the range of 3 to 20%, most preferably in the range of 5 to 20%.

Very particularly preferred catalysts are

1% to 25%, preferably 2% to 20%, preferably 3% to 20%, preferably 5% to 20% Pd/C, 1% to 25%, preferably 2% to 20%, preferably 3% to 20%, preferably 5% to 20% Pd/Al$_2$O$_3$, 1% to 25%, preferably 2% to 20%, preferably 3% to 20%, preferably 5% to 20% Pd(OH)$_2$/C, 1% to 25%, preferably 2% to 20%, preferably 3% to 20%, preferably 5% to 20% Palladium oxide/C, 1% to 25%, preferably 2% to 20%, preferably 3% to 20%, preferably 5% to 20% mixed Palladium oxide-hydroxide/C, 1% to 25%, preferably 2% to 20%, preferably 3% to 20%, preferably 5% to 20% Palladium oxide/$Al_2O_3$, 1% to 25%, preferably 2% to 20%, preferably 3% to 20%, preferably 5% to 20% mixed Palladium oxide-hydroxide/$Al_2O_3$, 1% to 25%, preferably 2% to 20%, preferably 3% to 20%, preferably 5% to 20% Palladium oxide/$SiO_2$, 1% to 25%, preferably 2% to 20%, preferably 3% to 20%, preferably 5% to 20% mixed Palladium oxide-hydroxide/$SiO_2$, 1% to 25%, preferably 2% to 20%, preferably 3% to 20%, preferably 5% to 20% Pd/$SiO_2$.

Very particularly preferred catalysts are 1% Pd/C, 1% Pd/$Al_2O_3$, 1% Pd(OH)$_2$/C, 1% Palladium oxide/C, 1% mixed Palladium oxide-hydroxide/C, 1% Palladium oxide/$Al_2O_3$, 1% mixed Palladium oxide-hydroxide/$Al_2O_3$, 1% Palladium oxide/$SiO_2$, 1% mixed Palladium oxide-hydroxide/$SiO_2$, 1% Pd/$SiO_2$.

Very particularly preferred catalysts are 2% Pd/C, 2% Pd/$Al_2O_3$, 2% Pd(OH)$_2$/C, 2% Palladium oxide/C, 2% mixed Palladium oxide-hydroxide/C, 2% Palladium oxide/$Al_2O_3$, 2% mixed Palladium oxide-hydroxide/$Al_2O_3$, 2% Palladium oxide/$SiO_2$, 2% mixed Palladium oxide-hydroxide/$SiO_2$, 2% Pd/$SiO_2$.

Very particularly preferred catalysts are 3% Pd/C, 3% Pd/$Al_2O_3$, 3% Pd(OH)$_2$/C, 3% Palladium oxide/C, 3% mixed Palladium oxide-hydroxide/C, 3% Palladium oxide/$Al_2O_3$, 3% mixed Palladium oxide-hydroxide/$Al_2O_3$, 3% Palladium oxide/$SiO_2$, 3% mixed Palladium oxide-hydroxide/$SiO_2$, 3% Pd/$SiO_2$.

Very particularly preferred catalysts are 4% Pd/C, 4% Pd/$Al_2O_3$, 4% Pd(OH)$_2$/C, 4% Palladium oxide/C, 4% mixed Palladium oxide-hydroxide/C, 4% Palladium oxide/$Al_2O_3$, 4% mixed Palladium oxide-hydroxide/$Al_2O_3$, 4% Palladium oxide/$SiO_2$, 4% mixed Palladium oxide-hydroxide/$SiO_2$, 4% Pd/$SiO_2$.

Very particularly preferred catalysts are 5% Pd/C, 5% Pd/$Al_2O_3$, 5% Pd(OH)$_2$/C, 5% Palladium oxide/C, 5% mixed Palladium oxide-hydroxide/C, 5% Palladium oxide/$Al_2O_3$, 5% mixed Palladium oxide-hydroxide/$Al_2O_3$, 5% Palladium oxide/$SiO_2$, 5% mixed Palladium oxide-hydroxide/$SiO_2$, 5% Pd/$SiO_2$.

Very particularly preferred catalysts are 7% Pd/C, 7% Pd/$Al_2O_3$, 7% Pd(OH)$_2$/C, 7% Palladium oxide/C, 7% mixed Palladium oxide-hydroxide/C, 7% Palladium oxide/$Al_2O_3$, 7% mixed Palladium oxide-hydroxide/$Al_2O_3$, 7% Palladium oxide/$SiO_2$, 7% mixed Palladium oxide-hydroxide/$SiO_2$, 7% Pd/$SiO_2$.

Very particularly preferred catalysts are 10% Pd/C, 10% Pd/$Al_2O_3$, 10% Pd(OH)$_2$/C, 10% Palladium oxide/C, 10% mixed Palladium oxide-hydroxide/C, 10% Palladium oxide/$Al_2O_3$, 10% mixed Palladium oxide-hydroxide/$Al_2O_3$, 10% Palladium oxide/$SiO_2$, 10% mixed Palladium oxide-hydroxide/$SiO_2$, 10% Pd/$SiO_2$.

Very particularly preferred catalysts are 15% Pd/C, 15% Pd/$Al_2O_3$, 15% Pd(OH)$_2$/C, 15% Palladium oxide/C, 15% mixed Palladium oxide-hydroxide/C, 15% Palladium oxide/$Al_2O_3$, 15% mixed Palladium oxide-hydroxide/$Al_2O_3$, 15% Palladium oxide/$SiO_2$, 15% mixed Palladium oxide-hydroxide/$SiO_2$, 15% Pd/$SiO_2$.

Very particularly preferred catalysts are 20% Pd/C, 20% Pd/$Al_2O_3$, 20% Pd(OH)$_2$/C, 20% Palladium oxide/C, 20% mixed Palladium oxide-hydroxide/C, 20% Palladium oxide/$Al_2O_3$, 20% mixed Palladium oxide-hydroxide/$Al_2O_3$, 20% Palladium oxide/$SiO_2$, 20% mixed Palladium oxide-hydroxide/$SiO_2$, 20% Pd/$SiO_2$.

Very particularly preferred catalysts are 25% Pd/C, 25% Pd/$Al_2O_3$, 25% Pd(OH)$_2$/C, 25% Palladium oxide/C, 25% mixed Palladium oxide-hydroxide/C, 25% Palladium oxide/$Al_2O_3$, 25% mixed Palladium oxide-hydroxide/$Al_2O_3$, 25% Palladium oxide/$SiO_2$, 25% mixed Palladium oxide-hydroxide/$SiO_2$, 25% Pd/$SiO_2$.

The catalysts are available from commercial sources like the companies BASF, Acros, Evonik.

The catalysts can be used in any form, for example dry, or wet (water-wet). Preferably, the catalysts are used several times. More preferably, the catalysts are used more than two times. Most preferably, the catalysts are used between two times and more. The catalysts can be used in a batch, semibatch or fixed bed hydrogenation reaction as well as in a continuous hydrogenation reaction process. More preferably the catalysts can be used in a batch or fixed bed hydrogenation reaction.

In the process according to the invention, the catalyst is used in an amount of about 0.01 mol % to about 50 mol % catalyst with respect to the amount of cyanopyridyl derivative according to formula (II). The catalyst is preferably used in an amount of about 0.1 to about 50 mol %, more preferably the catalyst is used in an amount of about 0.5 mol % to about 3 mol %.

Catalyst modifiers are such compounds which are capable of modifying the activity of the catalyst in such a way that the dehalogenation, in particular the dechlorination, of a halogen substituted, particularly chlorine substituted cyanopyridyl derivative according to formula (II) and (II'), as defined above, by forming the dehalogenated, particularly dechlorinated, corresponding compound of formula (II"), as defined above, is reduced compared to the reaction without the catalyst modifier. Whilst not being bound by theory, in the process of the present invention the modifier influences, in particular attenuates the activity of the metal catalyst, in particular of the palladium catalysts and thus reduces the formation of the unwanted dehalogenated, particularly the dechlorinated, side-products. One the one hand, this reduces the toxicity and on the other hand enhances the yield of the desired reaction products.

By using the catalyst modifier in the process of the present invention a reduction of the dehalogenated, particularly dechlorinated, side-products is achieved, preferably to equal or less than 25%, more preferably equal or less than 20%, even more preferably equal or less than 15%, particular more preferably equal or less than 10%, even particular more preferably equal or less than 5%, most preferably equal or less than 3%, most particular preferably equal or less than 1% can be achieved. It is in particular possible to reduce the amount of dehalogenated, particularly dechlorinated, side-products by a factor of at least 6, preferably of at least 10, more preferably of at least 30 compared to the respective reaction without using the modifier.

Suitable catalyst modifiers are organic or inorganic sulfur-containing compounds such as thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, $Na_2S_2O_3$-x$H_2O$, $Na_2S$, amines such as alkylamines, benzylamines, pyridines, morpholines, polyamines, amidines (e.g. chinoline); a inorganic or organic compounds comprising phosphor e.g. $PPh_3$; molybdenum containing compounds e.g. Mo(CO)$_6$ Vanadium oxides or sulfides e.g. V(V) oxide, V(IV) oxide, V(III) sulfide, $NH_4VO_3$; Lewis acids (e.g. $ZnBr_2$, $ZnCl_2$, $MgBr_2$, MgO, salts comprising Fe e.g. $FeCl_2$, $FeCl_3$, $Fe(OAc)_2$); tetraalkylammonium salts (e.g. iodides, bromides and chlorides) such as n-tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride; inorganic salts such as halides (e.g. NaCl, NaBr, NaI, KCl, KBr, KI, LiBr) or $MgBr_2$, $AlCl_3$, $CeCl_3$, CuCl, CuBr, CuI, $CuBr_2$, Suitable catalyst modifiers are organic or inorganic sulfur-containing compounds such as thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, $Na_2S_2O_3$-$xH_2O$, $Na_2S$; amines such chinoline, inorganic or organic compound comprising phosphor e.g. $PPh_3$; molybdenum containing compounds e.g. $Mo(CO)_6$, Vanadium oxides or sulfides e.g. V(V) oxide, V(IV) oxide, V(III) sulfide, $NH_4VO_3$; Lewis acids (e g $ZnBr_2$, $ZnCl_2$, $MgBr_2$, MgO, salts comprising Fe e.g. $FeCl_2$, $FeCl_3$, $Fe(OAc)_2$); tetraalkylammonium salts (e.g. iodides, bromides and chlorides) such as n-tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride; inorganic salts such as halides (e.g. NaCl, NaBr, NaI, KCl, KBr KI, LiBr) or $MgBr_2$, $AlCl_3$, $CeCl_3$, CuCl, CuBr, CuI, $CuBr_2$.

Suitable catalyst modifiers being organic sulfur-containing compounds are selected from the group consisting of thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, $Na_2S_2O_3$-$xH_2O$, $Na_2S$.

Preferred suitable catalyst modifiers being organic sulfur-containing compounds are selected from the group consisting of, tetrahydrothiophene, 2-mercaptophenol, cysteine, 3,6-dithia 1,8 octadiol, thiourea.

Preferred suitable catalyst modifiers being inorganic or organic compounds comprising phosphor are selected from the group consisting of $PPh_3$.

Preferred suitable catalyst modifiers being molybdenum containing compounds are selected from the group consisting of $Mo(CO)_6$ Preferred suitable catalyst modifiers being Vanadium oxides or sulfides are selected from the group consisting of V(V) oxide, V(IV) oxide, V(III) sulfide, $NH_4VO_3$.

Suitable catalyst modifiers being Lewis acids are selected from the group consisting of $ZnBr_2$, $ZnCl_2$, $MgBr_2$, MgO, Fe, $FeCl_2$, $FeCl_3$, $Fe(OAc)_2$.

Preferred suitable catalyst modifiers being Lewis acids are selected from the group consisting of $ZnBr_2$, $FeCl_3$, $Fe(OAc)_2$.

Suitable catalyst modifiers being tetraalkylammonium salts are selected from the group consisting of tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride.

Preferred suitable catalyst modifiers being tetraalkylammonium salts are selected from the group consisting of n-tetramethylammonium bromide (TMAB), n-tetrabutylammoniumbromide (TBAB).

Suitable catalyst modifiers being inorganic salts are selected from the group consisting of NaCl, NaBr, NaI, KCl, KBr, KI, LiBr, $MgBr_2$, $AlCl_3$, $CeCl_3$, CuCl, CuBr, CuI, $CuBr_2$.

Preferred suitable catalyst modifiers being inorganic salts are selected from the group consisting of NaBr, NaI, KBr, KI, CuI.

Suitable catalyst modifies being amines are alkylamines, benzylamines, pyridines, morpholines, polyamines, amidines (e.g. chinoline).

A preferred suitable catalyst modifier being amines is chinoline.

More preferred catalyst modifiers are selected from a) being organic sulfur-containing compounds selected from the group consisting of thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, $Na_2S_2O_3$-$xH_2O$, $Na_2S$;

b) being Vanadium oxides or sulfides selected from the group consisting of V(V) oxide, V(IV) oxide, V(III) sulfide, $NH_4VO_3$;

c) being inorganic or organic compounds comprising phosphor are selected from the group consisting of $PPh_3$;

d) being Lewis acids selected from the group consisting of $ZnBr_2$, $ZnCl_2$, $MgBr_2$, MgO, $FeCl_2$, $FeCl_3$, $Fe(OAc)_2$.

e) being tetraalkylammonium salts selected from the group consisting of tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride.

f) being inorganic salts selected from the group consisting of NaCl, NaBr, NaI, KCl, KBr, KI, LiBr, $MgBr_2$, $AlCl_3$, $CeCl_3$, CuCl, CuBr, CuI, $CuBr_2$, g) being molybdenum containing compounds selected from the group consisting of $Mo(CO)_6$, h) being amines selected from the group consisting of chinoline.

Even more preferred catalyst modifiers are selected from a) being organic sulfur-containing compounds selected from the group consisting of tetrahydrothiophene, 2-mercaptophenol, cysteine, 3,6-dithia 1,8 octadiol, thiourea, $Na_2S_2O_3$-$xH_2O$, $Na_2S$;

b) being Vanadium oxides or sulfides selected from the group consisting of V(V) oxide, V(IV) oxide, V(III) sulfide, $NH_4VO_3$;

c) being inorganic or organic compound comprising phosphor are selected from the group consisting of $PPh_3$, d) being Lewis acids selected from the group consisting of $ZnBr_2$, MgO, $FeCl_3$, $Fe(OAc)_2$;

e) being tetraalkylammonium salts selected from the group consisting of n-tetramethylammonium bromide (TMAB), n-tetrabutylammoniumbromide (TBAB);

f) being inorganic salts selected from the group consisting of NaBr, NaI, KBr, KI, CuI, g) being molybdenum containing compounds are selected from the group consisting of $Mo(CO)_6$, h) being amines selected from the group consisting of chinoline.

Preferred catalyst modifiers are sulfur-containing compounds, tetraalkylammonium halides, alkali halides and other metal halides. Further preferred catalyst modifiers are halide containing compounds, particularly such as selected from the halide containing catalyst modifier compounds as defined above. It is further preferred that the catalyst modifiers are selected from the group of aprotic compounds, i.e. from the compounds as listed herein, which cannot donate hydrogen.

More preferred catalyst modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, chinoline, n-tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride, tetrahydrothiophene, thioethanole, thio urea, V(V) oxide, V(IV) oxide, (V(III) sulfide, ZnBr$_2$.

Even more preferred catalyst modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, chinoline, n-tetramethylammonium bromide, n-tetraethylammonium bromide, n-tetrabutylammoniumbromide, tetrahydrothiophene, thioethanole, thio urea, V(V) oxide, V(IV) oxide, (V(III) sulfide, ZnBr$_2$ Even preferred modifiers are 3,6-dithia-1,8-octadiole, FeBr$_3$, FeCl$_3$, Fe(OAc)$_2$, KBr, MgBr$_2$, MgO, NaBr, NH$_4$VO$_3$, chinoline, n-tetramethylammonium bromide, n-tetraethylammonium bromide, n-tetrabutylammoniumbromide, tetrahydrothiophene, thioethanole, V(V) oxide, V(IV) oxide, ZnBr$_2$.

In one embodiment suitable modifiers are organic sulfur-containing compounds (e.g. thiophene, tetrahydrothiophene, 2,2'-thiobisethanol, diphenyl sulfide, thiophenol, thioanisole, sulfolane, thio urea, MgO, amines such as alkylamines, benzylamines, pyridines, morpholines, polyamines, amidines, phosphorous acids and its derivatives, metal ions and salts, or a combination of inorganic/organic phosphorous with a vanadium or molybdenum compound, Vanadium oxides or sulfides, NH$_4$VO$_3$, Lewis acids (e.g. ZnBr$_2$, ZnCl$_2$, MgBr$_2$, Fe or salts e.g. FeCl$_2$, FeCl$_3$, Fe(OAc)$_2$), tetraalkylammonium salts (e.g. iodides, bromides and chlorides) inorganic salts such as alkali halides (e.g. NaCl, NaBr, NaI, KCl, KBr KI, LiBr) or MgBr$_2$, AlCl$_3$, CeCl$_3$, CuCl, CuBr, CuI, CuBr$_2$.

In another embodiment modifiers are sulfur-containing compounds, tetraalkylammonium halides, alkali halides and other metal halides In another embodiment modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, n-tetramethylammonium iodide, n-tetraethylammonium iodide, n-tetrabutylammonium iodide, n-tetramethylammonium bromide, n-tetraethylammonium bromide, n-tetrabutylammoniumbromide, n-tetramethylammonium chloride, n-tetraethylammonium chloride, n-tetrabutylammoniumchloride, tetrahydrothiophene, thioethanole, thio urea, V(V) oxide, V(IV) oxide, (V(III) sulfide, ZnBr$_2$.

In another embodiment modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, n-tetramethylammonium bromide, n-tetraethylammonium bromide, n-tetrabutylammoniumbromide, tetrahydrothiophene, thioethanole, thio urea, V(V) oxide, V(IV) oxide, (V(III) sulfide, ZnBr$_2$ Even preferred modifiers are 3,6-dithia-1,8-octadiole, FeBr$_3$, FeCl$_3$, Fe(OAc)$_2$, KBr, MgBr$_2$, MgO, NaBr, NH$_4$VO$_3$, n-tetramethylammonium bromide, n-tetraethylammonium bromide, n-tetrabutylammoniumbromide, tetrahydrothiophene, thioethanole, V(V) oxide, V(IV) oxide, ZnBr$_2$.

In one embodiment the preferred amount of the modifier is in the range from about 0.0000001 equivalents to about 10 equivalents with respect to the amount of cyanopyridyl derivative according to formula (II) used in the reaction, more preferably in the range of 0.001 equivalents to 2 equivalents and even more preferably in the range of 0.01 equivalents to 0.2 equivalents and most preferably in the range of 0.1 equivalents to 0.2 equivalents.

In a further preferred embodiment of the invention from the definition of the catalyst modifier organic and inorganic acids are excluded. Therein, in particular, organic acids are excluded, more particularly acetic acid and sulfuric acid as well as sulfurous acid are excluded. It is even more preferred, that acetic acid is excluded from the definition of catalyst modifiers according to the present invention.

Further it is preferred that from the aforesaid preferred group of catalyst modifiers comprising sulfur-containing compounds, tetraalkylammonium halides, alkali halides and other metal halides organic and inorganic acids, particularly sulfur-containing acids are excluded.

In a further preferred embodiment of the present invention, a catalyst modifier is used, with organic and/or inorganic acids and/or one or more of the compounds of the group consisting of CuI, NaI, KI, thio urea and V(III) sulphide being excluded.

Whilst not being bound by theory, in the process of the present invention the acid is used to mask and thus protect the catalyst, in particular the palladium catalysts. During the hydrogenation reaction free amine compounds are formed which act as a catalyst poison and nearly immediately disable and inactivate the catalyst, thus significantly reducing the yield of the desired reaction products. By using an acid in the hydrogenation process of the present invention, higher recycling rates of the catalysts are possible, which further enhances the yield and an economic process management.

In addition, it was surprisingly found that the recycled catalysts can be masked and thus protected by substantially lower modifier amounts preferably in the range from about 0.0000001 equivalents to up to 0.05 equivalents with respect to the amount of cyanopyridyl derivative according to formula (II) used in the reaction, more preferably in the range of 0.0001 equivalents to 0.03 equivalents and even more preferably in the range of 0.001 equivalents to 0.02 equivalents. Therefore, a preferred process according to the invention is a process wherein the hydrogenation procedure is repeated under the same conditions as before with the exception that the catalyst is recycled and the modifier amount is in the last-mentioned ranges.

Suitable acids to be used in the hydrogenation reaction according to the invention are proton donating compounds. Preferred are organic acids such as acetic acid (CH$_3$CO$_2$H), trifluoro acetic acid (CF$_3$CO$_2$H), citric acid, p-toluenesulfonic acid, methanesulfonic acid, trifluoromethanesulfonic acid, formic acid or inorganic acids such as sulfuric acid (H$_2$SO$_4$), phosphoric acid (H$_3$PO$_4$).

Preferred acids for the hydrogenation reaction of step (A1) are selected from group consisting of acetic acid (CH$_3$CO$_2$H), methanesulfonic acid and H$_2$SO$_4$.

More preferred acids for the hydrogenation reaction of step (A1) are selected from group consisting of acetic acid (CH$_3$CO$_2$H) and H$_2$SO$_4$.

Mostly preferred acid for the hydrogenation reaction is H$_2$SO$_4$.

It is preferred to use the organic or inorganic acids as an additive in the hydrogenation reaction according to the invention in an amount of the acids in the range from about 0.1 equivalents to about 100 equivalents with respect to the amount of cyanopyridyl derivative according to formula (II) used in the reaction, more preferably in the range of 2 equivalents to about 10 equivalents and most preferably in the range of 0.5 equivalents to 2 equivalents.

In the additional steps following the hydrogenation reaction of step (A1) acids can optionally be added, too. In particular, in step (A3) optionally an acid can be added to the organic phase. Therein, the acids as defined above can be used, either alone or in mixtures thereof. Preferably, in step (A3) HCl or $H_2SO_4$ is used, either in aqueous and/or gaseous form. Therein, it is preferred to add the acid in an amount in the range of 0.1 equivalents to about 100 equivalents, more preferably in the range of 0.2 equivalents to about 10 equivalents, most preferably in the range of 0.5 equivalents to about 5 equivalents.

The hydrogenation reaction can be conducted at any suitable reaction conditions. In general the hydrogenation reaction will be conducted under batch, semi/batch or fixed bed conditions as well as in a continuous hydrogenation reaction process.

In one embodiment the hydrogenation reaction will be conducted under batch or fixed bed conditions.

Therein, the hydrogenation reaction is performed in either batch, semi-batch or continuous slurry reactors. Semi-batch hydrogenation involves the feeding of the nitrile (with or without acid and with or without modifier) to a slurry of catalyst in a solvent (or without). In this mode the ratio of nitrile to the catalyst is lower compared to batch process. In contrast to the batch or semi-batch process in the continuous mode the product is removed at the same rate as nitrile as is added.

According to the present invention the following combinations of catalyst, modifier and acid may be used:

TABLE 1

| Ref. | Catalyst | Ref. | Modifier | Ref. | Acid |
|---|---|---|---|---|---|
| c1 | Pd | m1 | Thiophene | a1 | Sulfuric acid |
| c2 | Pd/C | m2 | Tetrahydrothiophene | a2 | Phosphoric acid |
| c3 | Pd(OH)$_2$/C | m3 | 2-Mercaptophenol | a3 | Methanesulfonic acid |
| c4 | Pd/Al$_2$O$_3$ | m4 | Cysteine | | |
| c5 | Palladium oxide/C | m5 | 3,6-Dithia 1,8 octadiol | | |
| c6 | mixed Palladium oxide-hydroxide/C | m6 | 2,2'-Thiobisethanol | | |
| c7 | Palladium oxide/Al$_2$O$_3$ | m7 | Diphenyl sulfide | | |
| c8 | mixed Palladium oxide-hydroxide/Al$_2$O$_3$ | m8 | Thiophenol | | |
| c9 | Palladium/SiO$_2$ | m9 | Thioanisole | | |
| c10 | Palladium oxide/SiO$_2$ | m10 | Sulfolane | | |
| c11 | mixed Palladium oxide-hydroxide/SiO$_2$ | m11 | Thiourea | | |
| c12 | Pd/CaCO$_3$ | m12 | Na$_2$S$_2$O$_3$—xH$_2$O | | |
| c13 | Pd/C-diphenylsulfide | m13 | Na$_2$S | | |
| c14 | Pd/BaSO$_4$ | m14 | Chinoline | | |
| c15 | Pd(II)acetate-Polymethylhydrosiloxane | m15 | PPh$_3$ | | |
| c16 | Pd (Fe)/C | m16 | Mo(CO)$_6$ | | |
| c17 | Pd/C 5% sulfur | m17 | V(V) oxide | | |
| c18 | 5% Pd/0.5% V | m18 | V(IV) oxide | | |
| c19 | Pd/Pt | m19 | V(III) sulfide | | |
| | | m20 | NH$_4$VO$_3$ | | |
| | | m21 | ZnBr$_2$ | | |
| | | m22 | ZnCl$_2$ | | |
| | | m23 | MgBr$_2$ | | |
| | | m24 | MgO | | |
| | | m25 | FeCl$_2$ | | |
| | | m26 | FeCl$_3$ | | |
| | | m27 | Fe(OAc)$_2$) | | |
| | | m28 | n-Tetramethylammonium iodide | | |
| | | m29 | n-Tetraethylammonium iodide | | |
| | | m30 | n-Tetrabutylammonium iodide | | |
| | | m31 | n-Tetramethylammonium bromide (TMAB) | | |
| | | m32 | n-Tetraethylammonium bromide | | |
| | | m33 | n-Tetrabutylammoniumbromide (TBAB) | | |
| | | m34 | n-Tetramethylammonium chloride | | |
| | | m35 | n-Tetraethylammonium chloride | | |
| | | m36 | n-Tetrabutylammoniumchloride | | |
| | | m37 | NaCl | | |
| | | m38 | NaBr | | |
| | | m39 | NaI | | |
| | | m40 | KCl | | |
| | | m41 | KBr | | |
| | | m42 | KI | | |
| | | m43 | LiBr | | |
| | | m44 | MgBr$_2$ | | |
| | | m45 | AlCl$_3$ | | |
| | | m46 | CeCl$_3$ | | |
| | | m47 | CuCl | | |
| | | m48 | CuBr | | |
| | | m49 | CuI | | |
| | | m50 | CuBr$_2$ | | |
| | | m51 | BaSO$_4$ | | | c1+m1+a1, c1+m2+a1, c1+m3+a1, c1+m4+a1, c1+m5+a1, c1+m6+a1, c1+m7+a1, c1+m8+a1, c1+m9+a1, c1+m10+a1, c1+m11+a1, c1+m12+a1, c1+m13+a1, c1+m14+a1, c1+m15+a1, c1+m16+a1, c1+m17+a1, c1+m18+a1, c1+m19+a1, c1+m20+a1, c1+m21+a1, c1+m22+a1, c1+m23+a1, c1+m24+a1, c1+m25+a1, c1+m26+a1, c1+m27+a1, c1+m28+a1, c1+m29+a1, c1+m30+a1, c1+m31+a1, c1+m32+a1, c1+m33+a1, c1+m34+a1, c1+m35+a1, c1+m36+a1, c1+m37+a1, c1+m38+a1, c1+m39+a1, c1+m40+a1, c1+m41+a1, c1+m42+a1, c1+m43+a1, c1+m44+a1, c1+m45+a1, c1+m46+a1, c1+m47+a1, c1+m48+a1, c1+m49+a1, c1+m50+a1, c1+m51+a1, c1+m1+a2, c1+m2+a2, c1+m3+a2, c1+m4+a2, c1+m5+a2, c1+m6+a2, c1+m7+a2, c1+m8+a2, c1+m9+a2, c1+m10+a2, c1+m11+a2, c1+m12+a2, c1+m13+a2, c1+m14+a2, c1+m15+a2, c1+m16+a2, c1+m17+a2, c1+m18+a2, c1+m19+a2, c1+m20+a2, c1+m21+a2, c1+m22+a2, c1+m23+a2, c1+m24+a2, c1+m25+a2, c1+m26+a2, c1+m27+a2, c1+m28+a2, c1+m29+a2, c1+m30+a2, c1+m31+a2, c1+m32+a2, c1+m33+a2, c1+m34+a2, c1+m35+a2, c1+m36+a2, c1+m37+a2, c1+m38+a2, c1+m39+a2, c1+m40+a2, c1+m41+a2, c1+m42+a2, c1+m43+a2, c1+m44+a2, c1+m45+a2, c1+m46+a2, c1+m47+a2, c1+m48+a2, c1+m49+a2, c1+m50+a2, c1+m51+a2, c1+m1+a3, c1+m2+a3, c1+m3+a3, c1+m4+a3, c1+m5+a3, c1+m6+a3, c1+m7+a3, c1+m8+a3, c1+m9+a3, c1+m10+a3, c1+m11+a3, c1+m12+a3, c1+m13+a3, c1+m14+a3, c1+m15+a3, c1+m16+a3, c1+m17+a3, c1+m18+a3, c1+m19+a3, c1+m20+a3, c1+m21+a3, c1+m22+a3, c1+m23+a3, c1+m24+a3, c1+m25+a3, c1+m26+a3, c1+m27+a3, c1+m28+a3, c1+m29+a3, c1+m30+a3, c1+m31+a3, c1+m32+a3, c1+m33+a3, c1+m34+a3, c1+m35+a3, c1+m36+a3, c1+m37+a3, c1+m38+a3, c1+m39+a3, c1+m40+a3, c1+m41+a3, c1+m42+a3, c1+m43+a3, c1+m44+a3, c1+m45+a3, c1+m46+a3, c1+m47+a3, c1+m48+a3, c1+m49+a3, c1+m50+a3, c1+m51+a3, c2+m1+a1, c2+m2+a1, c2+m3+a1, c2+m4+a1, c2+m5+a1, c2+m6+a1, c2+m7+a1, c2+m8+a1, c2+m9+a1, c2+m10+a1, c2+m11+a1, c2+m12+a1, c2+m13+a1, c2+m14+a1, c2+m15+a1, c2+m16+a1, c2+m17+a1, c2+m18+a1, c2+m19+a1, c2+m20+a1, c2+m21+a1, c2+m22+a1, c2+m23+a1, c2+m24+a1, c2+m25+a1, c2+m26+a1, c2+m27+a1, c2+m28+a1, c2+m29+a1, c2+m30+a1, c2+m31+a1, c2+m32+a1, c2+m33+a1, c2+m34+a1, c2+m35+a1, c2+m36+a1, c2+m37+a1, c2+m38+a1, c2+m39+a1, c2+m40+a1, c2+m41+a1, c2+m42+a1, c2+m43+a1, c2+m44+a1, c2+m45+a1, c2+m46+a1, c2+m47+a1, c2+m48+a1, c2+m49+a1, c2+m50+a1, c2+m51+a1, c2+m1+a2, c2+m2+a2, c2+m3+a2, c2+m4+a2, c2+m5+a2, c2+m6+a2, c2+m7+a2, c2+m8+a2, c2+m9+a2, c2+m10+a2, c2+m11+a2, c2+m12+a2, c2+m13+a2, c2+m14+a2, c2+m15+a2, c2+m16+a2, c2+m17+a2, c2+m18+a2, c2+m19+a2, c2+m20+a2, c2+m21+a2, c2+m22+a2, c2+m23+a2, c2+m24+a2, c2+m25+a2, c2+m26+a2, c2+m27+a2, c2+m28+a2, c2+m29+a2, c2+m30+a2, c2+m31+a2, c2+m32+a2, c2+m33+a2, c2+m34+a2, c2+m35+a2, c2+m36+a2, c2+m37+a2, c2+m38+a2, c2+m39+a2, c2+m40+a2, c2+m41+a2, c2+m42+a2, c2+m43+a2, c2+m44+a2, c2+m45+a2, c2+m46+a2, c2+m47+a2, c2+m48+a2, c2+m49+a2, c2+m50+a2, c2+m51+a2, c2+m1+a3, c2+m2+a3, c2+m3+a3, c2+m4+a3, c2+m5+a3, c2+m6+a3, c2+m7+a3, c2+m8+a3, c2+m9+a3, c2+m10+a3, c2+m11+a3, c2+m12+a3, c2+m13+a3, c2+m14+a3, c2+m15+a3, c2+m16+a3, c2+m17+a3, c2+m18+a3, c2+m19+a3, c2+m20+a3, c2+m21+a3, c2+m22+a3, c2+m23+a3, c2+m24+a3, c2+m25+a3, c2+m26+a3, c2+m27+a3, c2+m28+a3, c2+m29+a3, c2+m30+a3, c2+m31+a3, c2+m32+a3, c2+m33+a3, c2+m34+a3, c2+m35+a3, c2+m36+a3, c2+m37+a3, c2+m38+a3, c2+m39+a3, c2+m40+a3, c2+m41+a3, c2+m42+a3, c2+m43+a3, c2+m44+a3, c2+m45+a3, c2+m46+a3, c2+m47+a3, c2+m48+a3, c2+m49+a3, c2+m50+a3, c2+m51+a3, c3+m1+a1, c3+m2+a1, c3+m3+a1, c3+m4+a1, c3+m5+a1, c3+m6+a1, c3+m7+a1, c3+m8+a1, c3+m9+a1, c3+m10+a1, c3+m11+a1, c3+m12+a1, c3+m13+a1, c3+m14+a1, c3+m15+a1, c3+m16+a1, c3+m17+a1, c3+m18+a1, c3+m19+a1, c3+m20+a1, c3+m21+a1, c3+m22+a1, c3+m23+a1, c3+m24+a1, c3+m25+a1, c3+m26+a1, c3+m27+a1, c3+m28+a1, c3+m29+a1, c3+m30+a1, c3+m31+a1, c3+m32+a1, c3+m33+a1, c3+m34+a1, c3+m35+a1, c3+m36+a1, c3+m37+a1, c3+m38+a1, c3+m39+a1, c3+m40+a1, c3+m41+a1, c3+m42+a1, c3+m43+a1, c3+m44+a1, c3+m45+a1, c3+m46+a1, c3+m47+a1, c3+m48+a1, c3+m49+a1, c3+m50+a1, c3+m51+a1, c3+m1+a2, c3+m2+a2, c3+m3+a2, c3+m4+a2, c3+m5+a2, c3+m6+a2, c3+m7+a2, c3+m8+a2, c3+m9+a2, c3+m10+a2, c3+m11+a2, c3+m12+a2, c3+m13+a2, c3+m14+a2, c3+m15+a2, c3+m16+a2, c3+m17+a2, c3+m18+a2, c3+m19+a2, c3+m20+a2, c3+m21+a2, c3+m22+a2, c3+m23+a2, c3+m24+a2, c3+m25+a2, c3+m26+a2, c3+m27+a2, c3+m28+a2, c3+m29+a2, c3+m30+a2, c3+m31+a2, c3+m32+a2, c3+m33+a2, c3+m34+a2, c3+m35+a2, c3+m36+a2, c3+m37+a2, c3+m38+a2, c3+m39+a2, c3+m40+a2, c3+m41+a2, c3+m42+a2, c3+m43+a2, c3+m44+a2, c3+m45+a2, c3+m46+a2, c3+m47+a2, c3+m48+a2, c3+m49+a2, c3+m50+a2, c3+m51+a2, c3+m1+a3, c3+m2+a3, c3+m3+a3, c3+m4+a3, c3+m5+a3, c3+m6+a3, c3+m7+a3, c3+m8+a3, c3+m9+a3, c3+m10+a3, c3+m11+a3, c3+m12+a3, c3+m13+a3, c3+m14+a3, c3+m15+a3, c3+m16+a3, c3+m17+a3, c3+m18+a3, c3+m19+a3, c3+m20+a3, c3+m21+a3, c3+m22+a3, c3+m23+a3, c3+m24+a3, c3+m25+a3, c3+m26+a3, c3+m27+a3, c3+m28+a3, c3+m29+a3, c3+m30+a3, c3+m31+a3, c3+m32+a3, c3+m33+a3, c3+m34+a3, c3+m35+a3, c3+m36+a3, c3+m37+a3, c3+m38+a3, c3+m39+a3, c3+m40+a3, c3+m41+a3, c3+m42+a3, c3+m43+a3, c3+m44+a3, c3+m45+a3, c3+m46+a3, c3+m47+a3, c3+m48+a3, c3+m49+a3, c3+m50+a3, c3+m51+a3, c4+m1+a1, c4+m2+a1, c4+m3+a1, c4+m4+a1, c4+m5+a1, c4+m6+a1, c4+m7+a1, c4+m8+a1, c4+m9+a1, c4+m10+a1, c4+m11+a1, c4+m12+a1, c4+m13+a1, c4+m14+a1, c4+m15+a1, c4+m16+a1, c4+m17+a1, c4+m18+a1, c4+m19+a1, c4+m20+a1, c4+m21+a1, c4+m22+a1, c4+m23+a1, c4+m24+a1, c4+m25+a1, c4+m26+a1, c4+m27+a1, c4+m28+a1, c4+m29+a1, c4+m30+a1, c4+m31+a1, c4+m32+a1, c4+m33+a1, c4+m34+a1, c4+m35+a1, c4+m36+a1, c4+m37+a1, c4+m38+a1, c4+m39+a1, c4+m40+a1, c4+m41+a1, c4+m42+a1, c4+m43+a1, c4+m44+a1, c4+m45+a1, c4+m46+a1, c4+m47+a1, c4+m48+a1, c4+m49+a1, c4+m50+a1, c4+m51+a1, c4+m1+a2, c4+m2+a2, c4+m3+a2, c4+m4+a2, c4+m5+a2, c4+m6+a2, c4+m7+a2, c4+m8+a2, c4+m9+a2, c4+m10+a2, c4+m11+a2, c4+m12+a2, c4+m13+a2, c4+m14+a2, c4+m15+a2, c4+m16+a2, c4+m17+a2, c4+m18+a2, c4+m19+a2, c4+m20+a2, c4+m21+a2, c4+m22+a2, c4+m23+a2, c4+m24+a2, c4+m25+a2, c4+m26+a2, c4+m27+a2, c4+m28+a2, c4+m29+a2, c4+m30+a2, c4+m31+a2, c4+m32+a2, c4+m33+a2, c4+m34+a2, c4+m35+a2, c4+m36+a2, c4+m37+a2, c4+m38+a2, c4+m39+a2, c4+m40+a2, c4+m41+a2, c4+m42+a2, c4+m43+a2, c4+m44+a2, c4+m45+a2, c4+m46+a2, c4+m47+a2, c4+m48+a2, c4+m49+a2, c4+m50+a2, c4+m51+a2, c4+m1+a3, c4+m2+a3, c4+m3+a3, c4+m4+a3, c4+m5+a3, c4+m6+a3, c4+m7+a3, c4+m8+a3, c4+m9+a3, c4+m10+a3, c4+m11+a3, c4+m12+a3, c4+m13+a3, c4+m14+a3, c4+m15+a3, c4+m16+a3, c4+m17+a3, c4+m18+a3, c4+m19+a3, c4+m20+a3, c4+m21+a3, c4+m22+a3, c4+m23+a3, c4+m24+a3, c4+m25+a3, c4+m26+a3, c4+m27+a3, c4+m28+a3, c4+m29+a3, c4+m30+a3, c4+m31+a3, c4+m32+a3, c4+m33+a3, c4+m34+a3, c4+m35+a3, c4+m36+a3, c4+m37+a3, c4+m38+a3, c4+m39+a3, c4+m40+a3, c4+m41+a3, c4+m42+a3, c4+m43+a3, c4+m44+a3, c4+m45+a3, c4+m46+a3, c4+m47+a3, c4+m48+a3, c4+m49+a3, c4+m50+a3, c4+m51+a3, c5+m1+a1, c5+m2+a1, c5+m3+a1, c5+m4+a1, c5+m5+a1, c5+m6+a1, c5+m7+a1, c5+m8+a1, c5+m9+a1, c5+m10+a1, c5+m11+a1, c5+m12+a1, c5+m13+a1, c5+m14+a1, c5+m15+a1, c5+m16+a1, c5+m17+a1, c5+m18+a1, c5+m19+a1, c5+m20+a1, c5+m21+a1, c5+m22+a1, c5+m23+a1, c5+m24+a1, c5+m25+a1, c5+m26+a1, c5+m27+a1, c5+m28+a1, c5+m29+a1, c5+m30+a1, c5+m31+a1, c5+m32+a1, c5+m33+a1, c5+m34+a1, c5+m35+a1, c5+m36+a1, c5+m37+a1, c5+m38+a1, c5+m39+a1, c5+m40+a1, c5+m41+a1, c5+m42+a1, c5+m43+a1, c5+m44+a1, c5+m45+a1, c5+m46+a1, c5+m47+a1, c5+m48+a1, c5+m49+a1, c5+m50+a1, c5+m51+a1, c5+m1+a2, c5+m2+a2, c5+m3+a2, c5+m4+a2, c5+m5+a2, c5+m6+a2, c5+m7+a2, c5+m8+a2, c5+m9+a2, c5+m10+a2, c5+m11+a2, c5+m12+a2, c5+m13+a2, c5+m14+a2, c5+m15+a2, c5+m16+a2, c5+m17+a2, c5+m18+a2, c5+m19+a2, c5+m20+a2, c5+m21+a2, c5+m22+a2, c5+m23+a2, c5+m24+a2, c5+m25+a2, c5+m26+a2, c5+m27+a2, c5+m28+a2, c5+m29+a2, c5+m30+a2, c5+m31+a2, c5+m32+a2, c5+m33+a2, c5+m34+a2, c5+m35+a2, c5+m36+a2, c5+m37+a2, c5+m38+a2, c5+m39+a2, c5+m40+a2, c5+m41+a2, c5+m42+a2, c5+m43+a2, c5+m44+a2, c5+m45+a2, c5+m46+a2, c5+m47+a2, c5+m48+a2, c5+m49+a2, c5+m50+a2, c5+m51+a2, c5+m1+a3, c5+m2+a3, c5+m3+a3, c5+m4+a3, c5+m5+a3, c5+m6+a3, c5+m7+a3, c5+m8+a3, c5+m9+a3, c5+m10+a3, c5+m11+a3, c5+m12+a3, c5+m13+a3, c5+m14+a3, c5+m15+a3, c5+m16+a3, c5+m17+a3, c5+m18+a3, c5+m19+a3, c5+m20+a3, c5+m21+a3, c5+m22+a3, c5+m23+a3, c5+m24+a3, c5+m25+a3, c5+m26+a3, c5+m27+a3, c5+m28+a3, c5+m29+a3, c5+m30+a3, c5+m31+a3, c5+m32+a3, c5+m33+a3, c5+m34+a3, c5+m35+a3, c5+m36+a3, c5+m37+a3, c5+m38+a3, c5+m39+a3, c5+m40+a3, c5+m41+a3, c5+m42+a3, c5+m43+a3, c5+m44+a3, c5+m45+a3, c5+m46+a3, c5+m47+a3, c5+m48+a3, c5+m49+a3, c5+m50+a3, c5+m51+a3, c6+m1+a1, c6+m2+a1, c6+m3+a1, c6+m4+a1, c6+m5+a1, c6+m6+a1, c6+m7+a1, c6+m8+a1, c6+m9+a1, c6+m10+a1, c6+m11+a1, c6+m12+a1, c6+m13+a1, c6+m14+a1, c6+m15+a1, c6+m16+a1, c6+m17+a1, c6+m18+a1, c6+m19+a1, c6+m20+a1, c6+m21+a1, c6+m22+a1, c6+m23+a1, c6+m24+a1, c6+m25+a1, c6+m26+a1, c6+m27+a1, c6+m28+a1, c6+m29+a1, c6+m30+a1, c6+m31+a1, c6+m32+a1, c6+m33+a1, c6+m34+a1, c6+m35+a1, c6+m36+a1, c6+m37+a1, c6+m38+a1, c6+m39+a1, c6+m40+a1, c6+m41+a1, c6+m42+a1, c6+m43+a1, c6+m44+a1, c6+m45+a1, c6+m46+a1, c6+m47+a1, c6+m48+a1, c6+m49+a1, c6+m50+a1, c6+m51+a1, c6+m1+a2, c6+m2+a2, c6+m3+a2, c6+m4+a2, c6+m5+a2, c6+m6+a2, c6+m7+a2, c6+m8+a2, c6+m9+a2, c6+m10+a2, c6+m11+a2, c6+m12+a2, c6+m13+a2, c6+m14+a2, c6+m15+a2, c6+m16+a2, c6+m17+a2, c6+m18+a2, c6+m19+a2, c6+m20+a2, c6+m21+a2, c6+m22+a2, c6+m23+a2, c6+m24+a2, c6+m25+a2, c6+m26+a2, c6+m27+a2, c6+m28+a2, c6+m29+a2, c6+m30+a2, c6+m31+a2, c6+m32+a2, c6+m33+a2, c6+m34+a2, c6+m35+a2, c6+m36+a2, c6+m37+a2, c6+m38+a2, c6+m39+a2, c6+m40+a2, c6+m41+a2, c6+m42+a2, c6+m43+a2, c6+m44+a2, c6+m45+a2, c6+m46+a2, c6+m47+a2, c6+m48+a2, c6+m49+a2, c6+m50+a2, c6+m51+a2, c6+m1+a3, c6+m2+a3, c6+m3+a3, c6+m4+a3, c6+m5+a3, c6+m6+a3, c6+m7+a3, c6+m8+a3, c6+m9+a3, c6+m10+a3, c6+m11+a3, c6+m12+a3, c6+m13+a3, c6+m14+a3, c6+m15+a3, c6+m16+a3, c6+m17+a3, c6+m18+a3, c6+m19+a3, c6+m20+a3, c6+m21+a3, c6+m22+a3, c6+m23+a3, c6+m24+a3, c6+m25+a3, c6+m26+a3, c6+m27+a3, c6+m28+a3, c6+m29+a3, c6+m30+a3, c6+m31+a3, c6+m32+a3, c6+m33+a3, c6+m34+a3, c6+m35+a3, c6+m36+a3, c6+m37+a3, c6+m38+a3, c6+m39+a3, c6+m40+a3, c6+m41+a3, c6+m42+a3, c6+m43+a3, c6+m44+a3, c6+m45+a3, c6+m46+a3, c6+m47+a3, c6+m48+a3, c6+m49+a3, c6+m50+a3, c6+m51+a3, c7+m1+a1, c7+m2+a1, c7+m3+a1, c7+m4+a1, c7+m5+a1, c7+m6+a1, c7+m7+a1, c7+m8+a1, c7+m9+a1, c7+m10+a1, c7+m11+a1, c7+m12+a1, c7+m13+a1, c7+m14+a1, c7+m15+a1, c7+m16+a1, c7+m17+a1, c7+m18+a1, c7+m19+a1, c7+m20+a1, c7+m21+a1, c7+m22+a1, c7+m23+a1, c7+m24+a1, c7+m25+a1, c7+m26+a1, c7+m27+a1, c7+m28+a1, c7+m29+a1, c7+m30+a1, c7+m31+a1, c7+m32+a1, c7+m33+a 1, c7+m34+a 1, c7+m35+a1, c7+m36+a1, c7+m37+a1, c7+m38+a1, c7+m39+a1, c7+m40+a1, c7+m41+a1, c7+m42+a1, c7+m43+a1, c7+m44+a1, c7+m45+a1, c7+m46+a1, c7+m47+a1, c7+m48+a1, c7+m49+a1, c7+m50+a1, c7+m51+a1, c7+m1+a2, c7+m2+a2, c7+m3+a2, c7+m4+a2, c7+m5+a2, c7+m6+a2, c7+m7+a2, c7+m8+a2, c7+m9+a2, c7+m10+a2, c7+m11+a2, c7+m12+a2, c7+m13+a2, c7+m14+a2, c7+m15+a2, c7+m16+a2, c7+m17+a2, c7+m18+a2, c7+m19+a2, c7+m20+a2, c7+m21+a2, c7+m22+a2, c7+m23+a2, c7+m24+a2, c7+m25+a2, c7+m26+a2, c7+m27+a2, c7+m28+a2, c7+m29+a2, c7+m30+a2, c7+m31+a2, c7+m32+a2, c7+m33+a2, c7+m34+a2, c7+m35+a2, c7+m36+a2, c7+m37+a2, c7+m38+a2, c7+m39+a2, c7+m40+a2, c7+m41+a2, c7+m42+a2, c7+m43+a2, c7+m44+a2, c7+m45+a2, c7+m46+a2, c7+m47+a2, c7+m48+a2, c7+m49+a2, c7+m50+a2, c7+m51+a2, c7+m1+a3, c7+m2+a3, c7+m3+a3, c7+m4+a3, c7+m5+a3, c7+m6+a3, c7+m7+a3, c7+m8+a3, c7+m9+a3, c7+m10+a3, c7+m11+a3, c7+m12+a3, c7+m13+a3, c7+m14+a3, c7+m15+a3, c7+m16+a3, c7+m17+a3, c7+m18+a3, c7+m19+a3, c7+m20+a3, c7+m21+a3, c7+m22+a3, c7+m23+a3, c7+m24+a3, c7+m25+a3, c7+m26+a3, c7+m27+a3, c7+m28+a3, c7+m29+a3, c7+m30+a3, c7+m31+a3, c7+m32+a3, c7+m33+a3, c7+m34+a3, c7+m35+a3, c7+m36+a3, c7+m37+a3, c7+m38+a3, c7+m39+a3, c7+m40+a3, c7+m41+a3, c7+m42+a3, c7+m43+a3, c7+m44+a3, c7+m45+a3, c7+m46+a3, c7+m47+a3, c7+m48+a3, c7+m49+a3, c7+m50+a3, c7+m51+a3, c8+m1+a1, c8+m2+a1, c8+m3+a1, c8+m4+a1, c8+m5+a1, c8+m6+a1, c8+m7+a1, c8+m8+a1, c8+m9+a1, c8+m10+a1, c8+m11+a1, c8+m12+a1, c8+m13+a1, c8+m14+a1, c8+m15+a1, c8+m16+a1, c8+m17+a1, c8+m18+a1, c8+m19+a1, c8+m20+a1, c8+m21+a1, c8+m22+a1, c8+m23+a1, c8+m24+a1, c8+m25+a1, c8+m26+a1, c8+m27+a1, c8+m28+a1, c8+m29+a1, c8+m30+a1, c8+m31+a1, c8+m32+a1, c8+m33+a1, c8+m34+a1, c8+m35+a1, c8+m36+a1, c8+m37+a1, c8+m38+a1, c8+m39+a1, c8+m40+a1, c8+m41+a1, c8+m42+a1, c8+m43+a1, c8+m44+a1, c8+m45+a1, c8+m46+a1, c8+m47+a1, c8+m48+a1, c8+m49+a1, c8+m50+a1, c8+m51+a1, c8+m1+a2, c8+m2+a2, c8+m3+a2, c8+m4+a2, c8+m5+a2, c8+m6+a2, c8+m7+a2, c8+m8+a2, c8+m9+a2, c8+m10+a2, c8+m11+a2, c8+m12+a2, c8+m13+a2, c8+m14+a2, c8+m15+a2, c8+m16+a2, c8+m17+a2, c8+m18+a2, c8+m19+a2, c8+m20+a2, c8+m21+a2, c8+m22+a2, c8+m23+a2, c8+m24+a2, c8+m25+a2, c8+m26+a2, c8+m27+a2, c8+m28+a2, c8+m29+a2, c8+m30+a2, c8+m31+a2, c8+m32+a2, c8+m33+a2, c8+m34+a2, c8+m35+a2, c8+m36+a2, c8+m37+a2, c8+m38+a2, c8+m39+a2, c8+m40+a2, c8+m41+a2, c8+m42+a2, c8+m43+a2, c8+m44+a2, c8+m45+a2, c8+m46+a2, c8+m47+a2, c8+m48+a2, c8+m49+a2, c8+m50+a2, c8+m51+a2, c8+m1+a3, c8+m2+a3, c8+m3+a3, c8+m4+a3, c8+m5+a3, c8+m6+a3, c8+m7+a3, c8+m8+a3, c8+m9+a3, c8+m10+a3, c8+m11+a3, c8+m12+a3, c8+m13+a3, c8+m14+a3, c8+m15+a3, c8+m16+a3, c8+m17+a3, c8+m18+a3, c8+m19+a3, c8+m20+a3, c8+m21+a3, c8+m22+a3, c8+m23+a3, c8+m24+a3, c8+m25+a3, c8+m26+a3, c8+m27+a3, c8+m28+a3, c8+m29+a3, c8+m30+a3, c8+m31+a3, c8+m32+a3, c8+m33+a3, c8+m34+a3, c8+m35+a3, c8+m36+a3, c8+m37+a3, c8+m38+a3, c8+m39+a3, c8+m40+a3, c8+m41+a3, c8+m42+a3, c8+m43+a3, c8+m44+a3, c8+m45+a3, c8+m46+a3, c8+m47+a3, c8+m48+a3, c8+m49+a3, c8+m50+a3, c8+m51+a3, c9+m1+a1, c9+m2+a1, c9+m3+a1, c9+m4+a1, c9+m5+a1, c9+m6+a1, c9+m7+a1, c9+m8+a1, c9+m9+a1, c9+m10+a1, c9+m11+a1, c9+m12+a1, c9+m13+a1, c9+m14+a1, c9+m15+a1, c9+m16+a1, c9+m17+a1, c9+m18+a1, c9+m19+a1, c9+m20+a1, c9+m21+a1, c9+m22+a1, c9+m23+a1, c9+m24+a1, c9+m25+a1, c9+m26+a1, c9+m27+a1, c9+m28+a1, c9+m29+a1, c9+m30+a1, c9+m31+a1, c9+m32+a1, c9+m33+a1, c9+m34+a1, c9+m35+a1, c9+m36+a1, c9+m37+a1, c9+m38+a1, c9+m39+a1, c9+m40+a1, c9+m41+a1, c9+m42+a1, c9+m43+a1, c9+m44+a1, c9+m45+a1, c9+m46+a1, c9+m47+a1, c9+m48+a1, c9+m49+a1, c9+m50+a1, c9+m51+a1, c9+m1+a2, c9+m2+a2, c9+m3+a2, c9+m4+a2, c9+m5+a2, c9+m6+a2, c9+m7+a2, c9+m8+a2, c9+m9+a2, c9+m10+a2, c9+m11+a2, c9+m12+a2, c9+m13+a2, c9+m14+a2, c9+m15+a2, c9+m16+a2, c9+m17+a2, c9+m18+a2, c9+m19+a2, c9+m20+a2, c9+m21+a2, c9+m22+a2, c9+m23+a2, c9+m24+a2, c9+m25+a2, c9+m26+a2, c9+m27+a2, c9+m28+a2, c9+m29+a2, c9+m30+a2, c9+m31+a2, c9+m32+a2, c9+m33+a2, c9+m34+a2, c9+m35+a2, c9+m36+a2, c9+m37+a2, c9+m38+a2, c9+m39+a2, c9+m40+a2, c9+m41+a2, c9+m42+a2, c9+m43+a2, c9+m44+a2, c9+m45+a2, c9+m46+a2, c9+m47+a2, c9+m48+a2, c9+m49+a2, c9+m50+a2, c9+m51+a2, c9+m1+a3, c9+m2+a3, c9+m3+a3, c9+m4+a3, c9+m5+a3, c9+m6+a3, c9+m7+a3, c9+m8+a3, c9+m9+a3, c9+m10+a3, c9+m11+a3, c9+m12+a3, c9+m13+a3, c9+m14+a3, c9+m15+a3, c9+m16+a3, c9+m17+a3, c9+m18+a3, c9+m19+a3, c9+m20+a3, c9+m21+a3, c9+m22+a3, c9+m23+a3, c9+m24+a3, c9+m25+a3, c9+m26+a3, c9+m27+a3, c9+m28+a3, c9+m29+a3, c9+m30+a3, c9+m31+a3, c9+m32+a3, c9+m33+a3, c9+m34+a3, c9+m35+a3, c9+m36+a3, c9+m37+a3, c9+m38+a3, c9+m39+a3, c9+m40+a3, c9+m41+a3, c9+m42+a3, c9+m43+a3, c9+m44+a3, c9+m45+a3, c9+m46+a3, c9+m47+a3, c9+m48+a3, c9+m49+a3, c9+m50+a3, c9+m51+a3, c10+m1+a1, c10+m2+a1, c10+m3+a1, c10+m4+a1, c10+m5+a1, c10+m6+a1, c10+m7+a1, c10+m8+a1, c10+m9+a1, c10+m10+a1, c10+m11+a1, c10+m12+a1, c10+m13+a1, c10+m14+a1, c10+m15+a1, c10+m16+a1, c10+m17+a1, c10+m18+a1, c10+m19+a1, c10+m20+a1, c10+m21+a1, c10+m22+a1, c10+m23+a1, c10+m24+a1, c10+m25+a1, c10+m26+a1, c10+m27+a1, c10+m28+a1, c10+m29+a1, c10+m30+a1, c10+m31+a1, c10+m32+a1, c10+m33+a1, c10+m34+a1, c10+m35+a1, c10+m36+a1, c10+m37+a1, c10+m38+a1, c10+m39+a1, c10+m40+a1, c10+m41+a1, c10+m42+a1, c10+m43+a1, c10+m44+a1, c10+m45+a1, c10+m46+a1, c10+m47+a1, c10+m48+a1, c10+m49+a1, c10+m50+a1, c10+m51+a1, c10+m1+a2, c10+m2+a2, c10+m3+a2, c10+m4+a2, c10+m5+a2, c10+m6+a2, c10+m7+a2, c10+m8+a2, c10+m9+a2, c10+m10+a2, c10+m11+a2, c10+m12+a2, c10+m13+a2, c10+m14+a2, c10+m15+a2, c10+m16+a2, c10+m17+a2, c10+m18+a2, c10+m19+a2, c10+m20+a2, c10+m21+a2, c10+m22+a2, c10+m23+a2, c10+m24+a2, c10+m25+a2, c10+m26+a2, c10+m27+a2, c10+m28+a2, c10+m29+a2, c10+m30+a2, c10+m31+a2, c10+m32+a2, c10+m33+a2, c10+m34+a2, c10+m35+a2, c10+m36+a2, c10+m37+a2, c10+m38+a2, c10+m39+a2, c10+m40+a2, c10+m41+a2, c10+m42+a2, c10+m43+a2, c10+m44+a2, c10+m45+a2, c10+m46+a2, c10+m47+a2, c10+m48+a2, c10+m49+a2, c10+m50+a2, c10+m51+a2, c10+m1+a3, c10+m2+a3, c10+m3+a3, c10+m4+a3, c10+m5+a3, c10+m6+a3, c10+m7+a3, c10+m8+a3, c10+m9+a3, c10+m10+a3, c10+m11+a3, c10+m12+a3, c10+m13+a3, c10+m14+a3, c10+m15+a3, c10+m16+a3, c10+m17+a3, c10+m18+a3, c10+m19+a3, c10+m20+a3, c10+m21+a3, c10+m22+a3, c10+m23+a3, c10+m24+a3, c10+m25+a3, c10+m26+a3, c10+m27+a3, c10+m28+a3, c10+m29+a3, c10+m30+a3, c10+m31+a3, c10+m32+a3, c10+m33+a3, c10+m34+a3, c10+m35+a3, c10+m36+a3, c10+m37+a3, c10+m38+a3, c10+m39+a3, c10+m40+a3, c10+m41+a3, c10+m42+a3, c10+m43+a3, c10+m44+a3, c10+m45+a3, c10+m46+a3, c10+m47+a3, c10+m48+a3, c10+m49+a3, c10+m50+a3, c10+m51+a3, c11+m1+a1, c11+m2+a1, c11+m3+a1, c11+m4+a1, c11+m5+a1, c11+m6+a1, c11+m7+a1, c11+m8+a1, c11+m9+a1, c11+m10+a1, c11+m11+a1, c11+m12+a1, c11+m13+a1, c11+m14+a1, c11+m15+a1, c11+m16+a1, c11+m17+a1, c11+m18+a1, c11+m19+a1, c11+m20+a1, c11+m21+a1, c11+m22+a1, c11+m23+a1, c11+m24+a1, c11+m25+a1, c11+m26+a1, c11+m27+a1, c11+m28+a1, c11+m29+a1, c11+m30+a1, c11+m31+a1, c11+m32+a1, c11+m33+a1, c11+m34+a1, c11+m35+a1, c11+m36+a1, c11+m37+a1, c11+m38+a1, c11+m39+a1, c11+m40+a1, c11+m41+a1, c11+m42+a1, c11+m43+a1, c11+m44+a1, c11+m45+a1, c11+m46+a1, c11+m47+a1, c11+m48+a1, c11+m49+a1, c11+m50+a1, c11+m51+a1, c11+m1+a2, c11+m2+a2, c11+m3+a2, c11+m4+a2, c11+m5+a2, c11+m6+a2, c11+m7+a2, c11+m8+a2, c11+m9+a2, c11+m10+a2, c11+m11+a2, c11+m12+a2, c11+m13+a2, c11+m14+a2, c11+m15+a2, c11+m16+a2, c11+m17+a2, c11+m18+a2, c11+m19+a2, c11+m20+a2, c11+m21+a2, c11+m22+a2, c11+m23+a2, c11+m24+a2, c11+m25+a2, c11+m26+a2, c11+m27+a2, c11+m28+a2, c11+m29+a2, c11+m30+a2, c11+m31+a2, c11+m32+a2, c11+m33+a2, c11+m34+a2, c11+m35+a2, c11+m36+a2, c11+m37+a2, c11+m38+a2, c11+m39+a2, c11+m40+a2, c11+m41+a2, c11+m42+a2, c11+m43+a2, c11+m44+a2, c11+m45+a2, c11+m46+a2, c11+m47+a2, c11+m48+a2, c11+m49+a2, c11+m50+a2, c11+m51+a2, c11+m1+a3, c11+m2+a3, c11+m3+a3, c11+m4+a3, c11+m5+a3, c11+m6+a3, c11+m7+a3, c11+m8+a3, c11+m9+a3, c11+m10+a3, c11+m11+a3, c11+m12+a3, c11+m13+a3, c11+m14+a3, c11+m15+a3, c11+m16+a3, c11+m17+a3, c11+m18+a3, c11+m19+a3, c11+m20+a3, c11+m21+a3, c11+m22+a3, c11+m23+a3, c11+m24+a3, c11+m25+a3, c11+m26+a3, c11+m27+a3, c11+m28+a3, c11+m29+a3, c11+ m30+a3, c11+m31+a3, c11+m32+a3, c11+m33+a3, c11+m34+a3, c11+m35+a3, c11+m36+a3, c11+m37+a3, c11+m38+a3, c11+m39+a3, c11+m40+a3, c11+m41+a3, c11+m42+a3, c11+m43+a3, c11+m44+a3, c11+m45+a3, c11+m46+a3, c11+m47+a3, c11+m48+a3, c11+m49+a3, c11+m50+a3, c11+m51+a3, c12+m1+a1, c12+m2+a1, c12+m3+a1, c12+m4+a1, c12+m5+a1, c12+m6+a1, c12+m7+a1, c12+m8+a1, c12+m9+a1, c12+m10+a1, c12+m11+a1, c12+m12+a1, c12+m13+a1, c12+m14+a1, c12+m15+a1, c12+m16+a1, c12+m17+a1, c12+m18+a1, c12+m19+a1, c12+m20+a1, c12+m21+a1, c12+m22+a1, c12+m23+a1, c12+m24+a1, c12+m25+a1, c12+m26+a1, c12+m27+a1, c12+m28+a1, c12+m29+a1, c12+m30+a1, c12+m31+a1, c12+m32+a1, c12+m33+a1, c12+m34+a1, c12+m35+a1, c12+m36+a1, c12+m37+a1, c12+m38+a1, c12+m39+a1, c12+m40+a1, c12+m41+a1, c12+m42+a1, c12+m43+a1, c12+m44+a1, c12+m45+a1, c12+m46+a1, c12+m47+a1, c12+m48+a1, c12+m49+a1, c12+m50+a1, c12+m51+a1, c12+m1+a2, c12+m2+a2, c12+m3+a2, c12+m4+a2, c12+m5+a2, c12+m6+a2, c12+m7+a2, c12+m8+a2, c12+m9+a2, c12+m10+a2, c12+m11+a2, c12+m12+a2, c12+m13+a2, c12+m14+a2, c12+m15+a2, c12+m16+a2, c12+m17+a2, c12+m18+a2, c12+m19+a2, c12+m20+a2, c12+m21+a2, c12+m22+a2, c12+m23+a2, c12+m24+a2, c12+m25+a2, c12+m26+a2, c12+m27+a2, c12+m28+a2, c12+m29+a2, c12+m30+a2, c12+m31+a2, c12+m32+a2, c12+m33+a2, c12+m34+a2, c12+m35+a2, c12+m36+a2, c12+m37+a2, c12+m38+a2, c12+m39+a2, c12+m40+a2, c12+m41+a2, c12+m42+a2, c12+m43+a2, c12+m44+a2, c12+m45+a2, c12+m46+a2, c12+m47+a2, c12+m48+a2, c12+m49+a2, c12+m50+a2, c12+m51+a2, c12+m1+a3, c12+m2+a3, c12+m3+a3, c12+m4+a3, c12+m5+a3, c12+m6+a3, c12+m7+a3, c12+m8+a3, c12+m9+a3, c12+m10+a3, c12+m11+a3, c12+m12+a3, c12+m13+a3, c12+m14+a3, c12+m15+a3, c12+m16+a3, c12+m17+a3, c12+m18+a3, c12+m19+a3, c12+m20+a3, c12+m21+a3, c12+m22+a3, c12+m23+a3, c12+m24+a3, c12+m25+a3, c12+m26+a3, c12+m27+a3, c12+m28+a3, c12+m29+a3, c12+m30+a3, c12+m31+a3, c12+m32+a3, c12+m33+a3, c12+m34+a3, c12+m35+a3, c12+m36+a3, c12+m37+a3, c12+m38+a3, c12+m39+a3, c12+m40+a3, c12+m41+a3, c12+m42+a3, c12+m43+a3, c12+m44+a3, c12+m45+a3, c12+m46+a3, c12+m47+a3, c12+m48+a3, c12+m49+a3, c12+m50+a3, c12+m51+a3, c13+m1+a1, c13+m2+a1, c13+m3+a1, c13+m4+a1, c13+m5+a1, c13+m6+a1, c13+m7+a1, c13+m8+a1, c13+m9+a1, c13+m10+a1, c13+m11+a1, c13+m12+a1, c13+m13+a1, c13+m14+a1, c13+m15+a1, c13+m16+a1, c13+m17+a1, c13+m18+a1, c13+m19+a1, c13+m20+a1, c13+m21+a1, c13+m22+a1, c13+m23+a1, c13+m24+a1, c13+m25+a1, c13+m26+a1, c13+m27+a1, c13+m28+a1, c13+m29+a1, c13+m30+a1, c13+m31+a1, c13+m32+a1, c13+m33+a1, c13+m34+a1, c13+m35+a1, c13+m36+a1, c13+m37+a1, c13+m38+a1, c13+m39+a1, c13+m40+a1, c13+m41+a1, c13+m42+a1, c13+m43+a1, c13+m44+a1, c13+m45+a1, c13+m46+a1, c13+m47+a1, c13+m48+a1, c13+m49+a1, c13+m50+a1, c13+m51+a1, c13+m1+a2, c13+m2+a2, c13+m3+a2, c13+m4+a2, c13+m5+a2, c13+m6+a2, c13+m7+a2, c13+m8+a2, c13+m9+a2, c13+m10+a2, c13+m11+a2, c13+m12+a2, c13+m13+a2, c13+m14+a2, c13+m15+a2, c13+m16+a2, c13+m17+a2, c13+m18+a2, c13+m19+a2, c13+m20+a2, c13+m21+a2, c13+m22+a2, c13+m23+a2, c13+m24+a2, c13+m25+a2, c13+m26+a2, c13+m27+a2, c13+m28+a2, c13+m29+a2, c13+m30+a2, c13+m31+a2, c13+m32+a2, c13+m33+a2, c13+m34+a2, c13+m35+a2, c13+m36+a2, c13+m37+a2, c13+m38+a2, c13+m39+a2, c13+m40+a2, c13+m41+a2, c13+m42+a2, c13+m43+a2, c13+m44+a2, c13+m45+a2, c13+m46+a2, c13+m47+a2, c13+m48+a2, c13+m49+a2, c13+m50+a2, c13+m51+a2, c13+m1+a3, c13+m2+a3, c13+m3+a3, c13+m4+a3, c13+m5+a3, c13+m6+a3, c13+m7+a3, c13+m8+a3, c13+m9+a3, c13+m10+a3, c13+m11+a3, c13+m12+a3, c13+m13+a3, c13+m14+a3, c13+m15+a3, c13+m16+a3, c13+m17+a3, c13+m18+a3, c13+m19+a3, c13+m20+a3, c13+m21+a3, c13+m22+a3, c13+m23+a3, c13+m24+a3, c13+m25+a3, c13+m26+a3, c13+m27+a3, c13+m28+a3, c13+m29+a3, c13+m30+a3, c13+m31+a3, c13+m32+a3, c13+m33+a3, c13+m34+a3, c13+m35+a3, c13+m36+a3, c13+m37+a3, c13+m38+a3, c13+m39+a3, c13+m40+a3, c13+m41+a3, c13+m42+a3, c13+m43+a3, c13+m44+a3, c13+m45+a3, c13+m46+a3, c13+m47+a3, c13+m48+a3, c13+m49+a3, c13+m50+a3, c13+m51+a3, c14+m1+a1, c14+m2+a1, c14+m3+a1, c14+m4+a1, c14+m5+a1, c14+m6+a1, c14+m7+a1, c14+m8+a1, c14+m9+a1, c14+m10+a1, c14+m11+a1, c14+m12+a1, c14+m13+a1, c14+m14+a1, c14+m15+a1, c14+m16+a1, c14+m17+a1, c14+m18+a1, c14+m19+a1, c14+m20+a1, c14+m21+a1, c14+m22+a1, c14+m23+a1, c14+m24+a1, c14+m25+a1, c14+m26+a1, c14+m27+a1, c14+m28+a1, c14+m29+a1, c14+m30+a1, c14+m31+a1, c14+m32+a1, c14+m33+a1, c14+m34+a1, c14+m35+a1, c14+m36+a1, c14+m37+a1, c14+m38+a1, c14+m39+a1, c14+m40+a1, c14+m41+a1, c14+m42+a1, c14+m43+a1, c14+m44+a1, c14+m45+a1, c14+m46+a1, c14+m47+a1, c14+m48+a1, c14+m49+a1, c14+m50+a1, c14+m51+a1, c14+m1+a2, c14+m2+a2, c14+m3+a2, c14+m4+a2, c14+m5+a2, c14+m6+a2, c14+m7+a2, c14+m8+a2, c14+m9+a2, c14+m10+a2, c14+m11+a2, c14+m12+a2, c14+m13+a2, c14+m14+a2, c14+m15+a2, c14+m16+a2, c14+m17+a2, c14+m18+a2, c14+m19+a2, c14+m20+a2, c14+m21+a2, c14+m22+a2, c14+m23+a2, c14+m24+a2, c14+m25+a2, c14+m26+a2, c14+m27+a2, c14+m28+a2, c14+m29+a2, c14+m30+a2, c14+m31+a2, c14+m32+a2, c14+m33+a2, c14+m34+a2, c14+m35+a2, c14+m36+a2, c14+m37+a2, c14+m38+a2, c14+m39+a2, c14+m40+a2, c14+m41+a2, c14+m42+a2, c14+m43+a2, c14+m44+a2, c14+m45+a2, c14+m46+a2, c14+m47+a2, c14+m48+a2, c14+m49+a2, c14+m50+a2, c14+m51+a2, c14+m1+a3, c14+m2+a3, c14+m3+a3, c14+m4+a3, c14+m5+a3, c14+m6+a3, c14+m7+a3, c14+m8+a3, c14+m9+a3, c14+m10+a3, c14+m11+a3, c14+m12+a3, c14+m13+a3, c14+m14+a3, c14+m15+a3, c14+m16+a3, c14+m17+a3, c14+m18+a3, c14+m19+a3, c14+m20+a3, c14+m21+a3, c14+m22+a3, c14+m23+a3, c14+m24+a3, c14+m25+a3, c14+m26+a3, c14+m27+a3, c14+m28+a3, c14+m29+a3, c14+m30+a3, c14+m31+a3, c14+m32+a3, c14+m33+a3, c14+m34+a3, c14+m35+a3, c14+m36+a3, c14+m37+a3, c14+m38+a3, c14+m39+a3, c14+m40+a3, c14+m41+a3, c14+m42+a3, c14+m43+a3, c14+m44+a3, c14+m45+a3, c14+m46+a3, c14+m47+a3, c14+m48+a3, c14+m49+a3, c14+m50+a3, c14+m51+a3, c15+m1+a1, c15+m2+a1, c15+m3+a1, c15+m4+a1, c15+m5+a1, c15+m6+a1, c15+m7+a1, c15+m8+a1, c15+m9+a1, c15+m10+a1, c15+m11+a1, c15+m12+a1, c15+m13+a1, c15+m14+a1, c15+m15+a1, c15+m16+a1, c15+m17+a1, c15+m18+a1, c15+m19+a1, c15+m20+a1, c15+m21+a1, c15+m22+a1, c15+m23+a1, c15+m24+a1, c15+m25+a1, c15+m26+a1, c15+m27+a1, c15+m28+a1, c15+m29+a1, c15+m30+a1, c15+m31+a1, c15+m32+a1, c15+m33+a1, c15+m34+a1, c15+m35+a1, c15+m36+a1, c15+m37+a1, c15+m38+a1, c15+m39+a1, c15+m40+a1, c15+m41+a1, c15+m42+a1, c15+m43+a1, c15+m44+a1, c15+m45+a1, c15+m46+a1, c15+m47+a1, c15+m48+a1, c15+m49+a1, c15+m50+a1, c15+m51+a1, c15+m1+a2, c15+m2+a2, c15+m3+a2, c15+m4+a2, c15+m5+a2, c15+m6+a2, c15+m7+a2, c15+m8+a2, c15+m9+a2, c15+m10+a2, c15+m11+a2, c15+m12+a2, c15+m13+a2, c15+m14+a2, c15+m15+a2, c15+m16+a2, c15+m17+a2, c15+m18+a2, c15+m19+a2, c15+m20+a2, c15+m21+a2, c15+m22+a2, c15+m23+a2, c15+m24+a2, c15+m25+a2, c15+m26+a2, c15+m27+a2, c15+m28+a2, c15+m29+a2, c15+m30+a2, c15+m31+a2, c15+m32+a2, c15+m33+a2, c15+m34+a2, c15+m35+a2, c15+m36+a2, c15+m37+a2, c15+m38+a2, c15+m39+a2, c15+m40+a2, c15+m41+a2, c15+m42+a2, c15+m43+a2, c15+m44+a2, c15+m45+a2, c15+m46+a2, c15+m47+a2, c15+m48+a2, c15+m49+a2, c15+m50+a2, c15+m51+a2, c15+m1+a3, c15+m2+a3, c15+m3+a3, c15+m4+a3, c15+m5+a3, c15+m6+a3, c15+m7+a3, c15+m8+a3, c15+m9+a3, c15+m10+a3, c15+m11+a3, c15+m12+a3, c15+m13+a3, c15+m14+a3, c15+m15+a3, c15+m16+a3, c15+m17+a3, c15+m18+a3, c15+m19+a3, c15+m20+a3, c15+m21+a3, c15+m22+a3, c15+m23+a3, c15+m24+a3, c15+m25+a3, c15+m26+a3, c15+m27+a3, c15+m28+a3, c15+m29+a3, c15+m30+a3, c15+m31+a3, c15+m32+a3, c15+m33+a3, c15+m34+a3, c15+m35+a3, c15+m36+a3, c15+m37+a3, c15+m38+a3, c15+m39+a3, c15+m40+a3, c15+m41+a3, c15+m42+a3, c15+m43+a3, c15+m44+a3, c15+m45+a3, c15+m46+a3, c15+m47+a3, c15+m48+a3, c15+m49+a3, c15+m50+a3, c15+m51+a3, c16+m1+a1, c16+m2+a1, c16+m3+a1, c16+m4+a1, c16+m5+a1, c16+m6+a1, c16+m7+a1, c16+m8+a1, c16+m9+a1, c16+m10+a1, c16+m11+a1, c16+m12+a1, c16+m13+a1, c16+m14+a1, c16+m15+a1, c16+m16+a1, c16+m17+a1, c16+m18+a1, c16+m19+a1, c16+m20+a1, c16+m21+a1, c16+m22+a1, c16+m23+a1, c16+m24+a1, c16+m25+a1, c16+m26+a1, c16+m27+a1, c16+m28+a1, c16+m29+a1, c16+m30+a1, c16+m31+a1, c16+m32+a1, c16+m33+a1, c16+m34+a1, c16+m35+a1, c16+m36+a1, c16+m37+a1, c16+m38+a1, c16+m39+a1, c16+m40+a1, c16+m41+a1, c16+m42+a1, c16+m43+a1, c16+m44+a1, c16+m45+a1, c16+m46+a1, c16+m47+a1, c16+m48+a1, c16+m49+a1, c16+m50+a1, c16+m51+a1, c16+m1+a2, c16+m2+a2, c16+m3+a2, c16+m4+a2, c16+m5+a2, c16+m6+a2, c16+m7+a2, c16+m8+a2, c16+m9+a2, c16+m10+a2, c16+m11+a2, c16+m12+a2, c16+m13+a2, c16+m14+a2, c16+m15+a2, c16+m16+a2, c16+m17+a2, c16+m18+a2, c16+m19+a2, c16+m20+a2, c16+m21+a2, c16+m22+a2, c16+m23+a2, c16+m24+a2, c16+m25+a2, c16+m26+a2, c16+m27+a2, c16+m28+a2, c16+m29+a2, c16+m30+a2, c16+m31+a2, c16+m32+a2, c16+m33+a2, c16+m34+a2, c16+m35+a2, c16+m36+a2, c16+m37+a2, c16+m38+a2, c16+m39+a2, c16+m40+a2, c16+m41+a2, c16+m42+a2, c16+m43+a2, c16+m44+a2, c16+m45+a2, c16+m46+a2, c16+m47+a2, c16+m48+a2, c16+m49+a2, c16+m50+a2, c16+m51+a2, c16+m1+a3, c16+m2+a3, c16+m3+a3, c16+m4+a3, c16+m5+a3, c16+m6+a3, c16+m7+a3, c16+m8+a3, c16+m9+a3, c16+m10+a3, c16+m11+a3, c16+m12+a3, c16+m13+a3, c16+m14+a3, c16+m15+a3, c16+m16+a3, c16+m17+a3, c16+m18+a3, c16+m19+a3, c16+m20+a3, c16+m21+a3, c16+m22+a3, c16+m23+a3, c16+m24+a3, c16+m25+a3, c16+m26+a3, c16+m27+a3, c16+m28+a3, c16+m29+a3, c16+m30+a3, c16+m31+a3, c16+m32+a3, c16+m33+a3, c16+m34+a3, c16+m35+a3, c16+m36+a3, c16+m37+a3, c16+m38+a3, c16+m39+a3, c16+m40+a3, c16+m41+a3, c16+m42+a3, c16+m43+a3, c16+m44+a3, c16+m45+a3, c16+m46+a3, c16+m47+a3, c16+m48+a3, c16+m49+a3, c16+m50+a3, c16+m51+a3, c17+m1+a1, c17+m2+a1, c17+m3+a1, c17+m4+a1, c17+m5+a1, c17+m6+a1, c17+m7+a1, c17+m8+a1, c17+m9+a1, c17+m10+a1, c17+m11+a1, c17+m12+a1, c17+m13+a1, c17+m14+a1, c17+m15+a1, c17+m16+a1, c17+m17+a1, c17+m18+a1, c17+m19+a1, c17+m20+a1, c17+m21+a1, c17+m22+a1, c17+m23+a1, c17+m24+a1, c17+m25+a1, c17+m26+a1, c17+m27+a1, c17+m28+a1, c17+m29+a1, c17+m30+a1, c17+m31+a1, c17+m32+a1, c17+m33+a1, c17+m34+a1, c17+m35+a1, c17+m36+a1, c17+m37+a1, c17+m38+a1, c17+m39+a1, c17+m40+a1, c17+m41+a1, c17+m42+a1, c17+m43+a1, c17+m44+a1, c17+m45+a1, c17+m46+a1, c17+m47+a1, c17+m48+a1, c17+m49+a1, c17+m50+a1, c17+m51+a1, c17+m1+a2, c17+m2+a2, c17+m3+a2, c17+m4+a2, c17+m5+a2, c17+m6+a2, c17+m7+a2, c17+m8+a2, c17+m9+a2, c17+m10+a2, c17+m11+a2, c17+m12+a2, c17+m13+a2, c17+m14+a2, c17+m15+a2, c17+m16+a2, c17+m17+a2, c17+m18+a2, c17+m19+a2, c17+m20+a2, c17+m21+a2, c17+m22+a2, c17+m23+a2, c17+m24+a2, c17+m25+a2, c17+m26+a2, c17+m27+a2, c17+m28+a2, c17+m29+a2, c17+m30+a2, c17+m31+a2, c17+m32+a2, c17+m33+a2, c17+m34+a2, c17+m35+a2, c17+m36+a2, c17+m37+a2, c17+m38+a2, c17+m39+a2, c17+m40+a2, c17+m41+a2, c17+m42+a2, c17+m43+a2, c17+m44+a2, c17+m45+a2, c17+m46+a2, c17+m47+a2, c17+m48+a2, c17+m49+a2, c17+m50+a2, c17+m51+a2, c17+m1+a3, c17+m2+a3, c17+m3+a3, c17+m4+a3, c17+m5+a3, c17+m6+a3, c17+m7+a3, c17+m8+a3, c17+m9+a3, c17+m10+a3, c17+m11+a3, c17+m12+a3, c17+m13+a3, c17+m14+a3, c17+m15+a3, c17+m16+a3, c17+m17+a3, c17+m18+a3, c17+m19+a3, c17+m20+a3, c17+m21+a3, c17+m22+a3, c17+m23+a3, c17+m24+a3, c17+m25+a3, c17+m26+a3, c17+m27+a3, c17+m28+a3, c17+m29+a3, c17+m30+a3, c17+m31+a3, c17+m32+a3, c17+m33+a3, c17+m34+a3, c17+m35+a3, c17+m36+a3, c17+m37+a3, c17+m38+a3, c17+m39+a3, c17+m40+a3, c17+m41+a3, c17+m42+a3, c17+m43+a3, c17+m44+a3, c17+m45+a3, c17+m46+a3, c17+m47+a3, c17+m48+a3, c17+m49+a3, c17+m50+a3, c17+m51+a3, c18+m1+a1, c18+m2+a1, c18+m3+a1, c18+m4+a1, c18+m5+a1, c18+m6+a1, c18+m7+a1, c18+m8+a1, c18+m9+a1, c18+m10+a1, c18+m11+a1, c18+m12+a1, c18+m13+a1, c18+m14+a1, c18+m15+a1, c18+m16+a1, c18+m17+a1, c18+m18+a1, c18+m19+a1, c18+m20+a1, c18+m21+a1, c18+m22+a1, c18+m23+a1, c18+m24+a1, c18+m25+a1, c18+m26+a1, c18+m27+a1, c18+m28+a1, c18+m29+a1, c18+m30+a1, c18+m31+a1, c18+m32+a1, c18+m33+a1, c18+m34+a1, c18+m35+a1, c18+m36+a1, c18+m37+a1, c18+m38+a1, c18+m39+a1, c18+m40+a1, c18+m41+a1, c18+m42+a1, c18+m43+a1, c18+m44+a1, c18+m45+a1, c18+m46+a1, c18+m47+a1, c18+m48+a1, c18+m49+a1, c18+m50+a1, c18+m51+a1, c18+m1+a2, c18+m2+a2, c18+m3+a2, c18+m4+a2, c18+m5+a2, c18+m6+a2, c18+m7+a2, c18+m8+a2, c18+m9+a2, c18+m10+a2, c18+m11+a2, c18+m12+a2, c18+m13+a2, c18+m14+a2, c18+m15+a2, c18+m16+a2, c18+m17+a2, c18+m18+a2, c18+m19+a2, c18+m20+a2, c18+m21+a2, c18+m22+a2, c18+m23+a2, c18+m24+a2, c18+m25+a2, c18+m26+a2, c18+m27+a2, c18+m28+a2, c18+m29+a2, c18+m30+a2, c18+m31+a2, c18+m32+a2, c18+m33+a2, c18+m34+a2, c18+m35+a2, c18+m36+a2, c18+m37+a2, c18+m38+a2, c18+m39+a2, c18+m40+a2, c18+m41+a2, c18+m42+a2, c18+m43+a2, c18+m44+a2, c18+m45+a2, c18+m46+a2, c18+m47+a2, c18+m48+a2, c18+m49+a2, c18+m50+a2, c18+m51+a2, c18+m1+a3, c18+m2+a3, c18+m3+a3, c18+m4+a3, c18+m5+a3, c18+m6+a3, c18+m7+a3, c18+m8+a3, c18+m9+a3, c18+m10+a3, c18+m11+a3, c18+m12+a3, c18+m13+a3, c18+m14+a3, c18+m15+a3, c18+m16+a3, c18+m17+a3, c18+m18+a3, c18+m19+a3, c18+m20+a3, c18+m21+a3, c18+m22+a3, c18+m23+a3, c18+m24+a3, c18+m25+a3, c18+m26+a3, c18+m27+a3, c18+m28+a3, c18+m29+a3, c18+m30+a3, c18+m31+a3, c18+m32+a3, c18+m33+a3, c18+m34+a3, c18+m35+a3, c18+m36+a3, c18+m37+a3, c18+ m38+a3, c18+m39+a3, c18+m40+a3, c18+m41+a3, c18+m42+a3, c18+m43+a3, c18+m44+a3, c18+m45+a3, c18+m46+a3, c18+m47+a3, c18+m48+a3, c18+m49+a3, c18+m50+a3, c18+m51+a3,
c19+m1+a1, c19+m2+a1, c19+m3+a1, c19+m4+a1, c19+m5+a1, c19+m6+a1, c19+m7+a1, c19+m8+a1, c19+m9+a1, c19+m10+a1, c19+m11+a1, c19+m12+a1, c19+m13+a1, c19+m14+a1, c19+m15+a1, c19+m16+a1, c19+m17+a1, c19+m18+a1, c19+m19+a1, c19+m20+a1, c19+m21+a1, c19+m22+a1, c19+m23+a1, c19+m24+a1, c19+m25+a1, c19+m26+a1, c19+m27+a1, c19+m28+a1, c19+m29+a1, c19+m30+a1, c19+m31+a1, c19+m32+a1, c19+m33+a1, c19+m34+a1, c19+m35+a1, c19+m36+a1, c19+m37+a1, c19+m38+a1, c19+m39+a1, c19+m40+a1, c19+m41+a1, c19+m42+a1, c19+m43+a1, c19+m44+a1, c19+m45+a1, c19+m46+a1, c19+m47+a1, c19+m48+a1, c19+m49+a1, c19+m50+a1, c19+m51+a1, c19+m1+a2, c19+m2+a2, c19+m3+a2, c19+m4+a2, c19+m5+a2, c19+m6+a2, c19+m7+a2, c19+m8+a2, c19+m9+a2, c19+m10+a2, c19+m11+a2, c19+m12+a2, c19+m13+a2, c19+m14+a2, c19+m15+a2, c19+m16+a2, c19+m17+a2, c19+m18+a2, c19+m19+a2, c19+m20+a2, c19+m21+a2, c19+m22+a2, c19+m23+a2, c19+m24+a2, c19+m25+a2, c19+m26+a2, c19+m27+a2, c19+m28+a2, c19+m29+a2, c19+m30+a2, c19+m31+a2, c19+m32+a2, c19+m33+a2, c19+m34+a2, c19+m35+a2, c19+m36+a2, c19+m37+a2, c19+m38+a2, c19+m39+a2, c19+m40+a2, c19+m41+a2, c19+m42+a2, c19+m43+a2, c19+m44+a2, c19+m45+a2, c19+m46+a2, c19+m47+a2, c19+m48+a2, c19+m49+a2, c19+m50+a2, c19+m51+a2, c19+m1+a3, c19+m2+a3, c19+m3+a3, c19+m4+a3, c19+m5+a3, c19+m6+a3, c19+m7+a3, c19+m8+a3, c19+m9+a3, c19+m10+a3, c19+m11+a3, c19+m12+a3, c19+m13+a3, c19+m14+a3, c19+m15+a3, c19+m16+a3, c19+m17+a3, c19+m18+a3, c19+m19+a3, c19+m20+a3, c19+m21+a3, c19+m22+a3, c19+m23+a3, c19+m24+a3, c19+m25+a3, c19+m26+a3, c19+m27+a3, c19+m28+a3, c19+m29+a3, c19+m30+a3, c19+m31+a3, c19+m32+a3, c19+m33+a3, c19+m34+a3, c19+m35+a3, c19+m36+a3, c19+m37+a3, c19+m38+a3, c19+m39+a3, c19+m40+a3, c19+m41+a3, c19+m42+a3, c19+m43+a3, c19+m44+a3, c19+m45+a3, c19+m46+a3, c19+m47+a3, c19+m48+a3, c19+m49+a3, c19+m50+a3, c19+m51+a3,

Pressure

The catalytic hydrogenation according to the invention is preferably performed under elevated pressure (i.e. up to about 600 bar), preferably in an autoclave in a hydrogen gas atmosphere, preferably in a semi batch hydrogenation process. The (additional) pressure increase can be brought about by supply of an inert gas, such as nitrogen or argon. The hydrogenation according to the invention is effected preferably at a hydrogen pressure in the range from about 0 to about 300 bar, more preferably at a hydrogen pressure in the range from about 5 to about 200 bar. Preferred ranges of hydrogen pressure are also e from about 0.5 to about 150 bar.

In one embodiment the catalytic hydrogenation according to the invention is preferably performed under elevated pressure (i.e. up to about 200 bar).

The hydrogen pressure according to the invention can also vary during the process.

If necessary, suitable measures for dissipating heat from the exothermic reaction can be applied.

Temperature

The catalytic hydrogenation according to the invention is performed preferably at a temperature in the range from about −20° C. to about 200° C., more preferably at a temperature in the range from about 0° C. to about 100° C., most preferably in the range from about 5 to 70° C.

Solvents

The catalytic hydrogenation can also be performed without a solvent. However, it is generally advantageous to perform the process according to the invention in the presence of solvents (diluents).

Solvents are advantageously used in such an amount that the reaction mixture remains efficiently stirrable over the entire process. Advantageously, based on the nitrile used, 1 to 50 times the amount of solvent, preferably 2 to 40 times the amount of solvent and more preferably 2 to 30 times the amount of solvent is used.

Useful solvents for the performance of the hydrogenation process according to the invention include water and all organic solvents which are inert under the reaction conditions, the type of solvent used depending on the type of reaction procedure, more particularly on the type of catalyst used and/or the hydrogen source (introduction of gaseous hydrogen or generation in situ). Solvents are also understood in accordance with the invention to mean mixtures of pure solvents.

Solvents suitable in accordance to the invention are water, acids such as acetic acid, acetic anhydride, alcohols such as methanol, ethanol, isopropanol, butanol, t-amyl alcohol, benzyl alcohol, 1,3-butanediol, 1,4-butanediol, 2-butoxyethanol, cyclohexanol, diethylene glycol, diethylen glycol methyl ether, dipropylene glycol, dipropylene glycol methyl ether, 2-ethoxyethanol, ethanolamine, ethylene glycol, glycerol, hexanole, hexylene glycol, isoamyl alcohol, isobutanol, 2-methoxyethanol, 1-octanol, pentanol, propylene glycol, tetraethylene glycol, triethylene glycol; ethers, such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyl tetrahydrofuran, methyl cyclopenthylether, dioxane, dichlorodiethyl ether, petroleum ether, ligroin and polyethers of ethylene oxide and/or propylene oxide; ketones such as acetone, cyclohexanone, 3-pentanone, amines, such as trimethyl-, triethyl-, tripropyl-, and tributylamine, tert-amyl methyl ether (TAME), N-methyl morpholine, aliphatic, cycloaliphatic or aromatic hydrocarbons such as pentane, hexane, methyl cyclohexane heptane, octane, nonane, and technical-grade hydrocarbons which may be substituted by fluorine and chlorine atoms, such as dichloromethane, fluorobenzene, chlorobenzene or dichlorobenzene, for example white spirits having components with boiling points in the range, for example, from 40° C. to 250° C., cymene, petroleum fractions within a boiling range from 70° C. to 190° C., toluene, xylenes, ethylbenzene. esters such as amyl acetates, butyl acetates, ethyl acetate, isobutyl acetate, isopropyl acetate, 2-methoxyethyl acetate, methyl acetate, propyl acetate, prop glycol methyl ether acetate, carbonate such as propylene carbonate, dimethyl carbonate, diethyl carbonate; N,N-Dimethylacetimide, N,N-Dimethylformamide, 2-pyrrolidone and N-methyl pyrrolidone.

In the process according to the invention, it is preferred to use alcohols or cyclic ethers as solvent. Preferred is methanol, ethanol, isopropanol, t-butanol, tetrahydrofuran, or methyltetrahydrofuran. Among before mentioned solvents methanol is preferred. It is further preferred that from the group of suitable solvents to be used in the hydrogenation reaction acids such as acetic acid and acetic anhydride are excluded.

The solvents, which may be used in the additional process steps following the hydrogenation step (A1) may be independently selected from the solvents as defined above for the hydrogenation step (A1).

The solvents which can be used in step (A1), (A3) and (A4) can be the same or different and can independently in each case be used as mixtures of solvents, in particular mixtures comprising water or as solvents consisting of only one component.

The reaction conditions for step (B1) may be independently selected from the reaction conditions as defined above for the step (A1).

Suitable bases for step (B1a) are inorganic such $Na_2CO_3$, $NaHCO_3$, $K_2CO_3$, $KHCO_3$, NaOH, KOH, $Ca(OH)_2$, $Mg(OH)_2$ or organic bases such as triethyl amine, N,N-diisopropylethylamine. Particularly preferred for step (B1a) are $Na_2CO_3$, $K_2CO_3$, NaOH, KOH and $Ca(OH)_2$. More preferred are NaOH, KOH, $Ca(OH)_2$. Mostly preferred are NaOH, KOH. Preferably, in step (B1a) a base as defined herein is added to the reaction mixture comprising the 2-methylaminopyridine derivative of formula (III) after filtering off the catalyst to adjust the pH to a value of pH 4 to 12, more preferably to a value of 6 to 9.

Suitable solvents for the step (B2) are alcohols such as methanol, ethanol, iso-propanol, propanol, n-butanol, iso-butanol, t-pentanol, benzyl alcohol, 1,3-butanediol, 1,4-butandiol, 2-butoxyethanol, cyclohexanol, diethylene glycol, diethylen glycol methyl ether, dipropylene glycol, dipropylene glycol methyl ether, 2-ethoxyethanol, ethylene glycol, glycerol, hexanole, hexylene glycol, isopentanol, isobutanol, 2-methoxyethanol, 1-octanol, pentanol, propylene glycol, tetraethylene glycol, triethylene glycol; ethers, such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyl tetrahydrofuran, methyl cyclopenthylether, dioxane, dichlorodiethyl ether, petroleum ether, ligroin and polyethers of ethylene oxide and/or propylene oxide; hydrocarbons such as toluene, xylenes, ethylbenzene, or other solvents such as water or N,N-Dimethylacetimide, N,N-Dimethylformamide, 2-pyrrolidone and N-methyl pyrrolidone. Preferred are water and alcohols such as methanol, ethanol, iso-propanol, propanol, n-butanol, iso-butanol. Particularly preferred are water and methanol.

Suitable bases for the step (B2) are inorganic bases such as $Na_2CO_3$, $NaHCO_3$, $K_2CO_3$, $KHCO_3$, NaOH, KOH, $Ca(OH)_2$. Preferred are NaOH, KOH, $Ca(OH)_2$. Mostly preferred are NaOH and KOH.

The process step (B2) is performed preferably at a temperature in the range from about 0° C. to about +150° C., more preferably at a temperature in the range from about +10° C. to about +100° C., most preferably in the range from about +20° C. to +50° C.

Suitable acids for step (B3) are inorganic acids such as hydrochloric acid (HCl), sulfuric acid ($H_2SO_4$), phosphoric acid ($H_3PO_4$) or organic acids such as acetic acid ($CH_3CO_2H$), trifluoro acetic acid ($CF_3CO_2H$), citric acid, p-toluenesulfonic acid, methanesulfonic acid, trifluoromethanesulfonic acid, formic acid. Preferably, in step (B3) an acid as defined herein is added to the reaction mixture to adjust the pH to a value of 1 to 6, very preferably to a value of 2 to 4.

Suitable solvents for step (B4) are ethers such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyl tetrahydrofuran, methyl cyclopenthylether, dioxane, dichlorodiethyl ether, petroleum ether, ligroin and polyethers of ethylene oxide and/or propylene oxide, hydrocarbons such as hexane, cyclohexane, methylcyclohexane, benzene, toluene or xylene, halohydrocarbons such as dichloromethane, trichloromethane, tetrachloromethane, trichloroethane, 1,2-dichloroethane, chlorobenzene or chlorotoluene. Preferred are hydrocarbons such as hexane, cyclohexane, methylcyclohexane, benzene, toluene or xylene. Particularly preferred are cyclohexane and methylcyclohexane.

Preferably the hydrogenation step (A1) or (B1) is performed in the presence of a metal catalyst, a catalyst modifier, and the acid $H_2SO_4$ in the solvent methanol, wherein the amount of the catalyst modifier is in the range from about 0.0000001 equivalents to about 10 equivalents with respect to the amount of cyanopyridyl derivative according to formula (II).

More preferably the hydrogenation step (A1) or (B1) is performed in the presence of a metal catalyst, a catalyst modifier, and the acid $H_2SO_4$ in the solvent methanol, wherein the amount of the catalyst modifier is in the range from about 0.001 equivalents to about 2 equivalents with respect to the amount of cyanopyridyl derivative according to formula (II).

Even more preferably the hydrogenation step (A1) or (B1) is performed in the presence of a metal catalyst, a catalyst modifier, and the acid $H_2SO_4$ in the solvent methanol, wherein the amount of the catalyst modifier is in the range from about 0.01 equivalents to about 0.2 equivalents with respect to the amount of cyanopyridyl derivative according to formula (II).

Particular preferably the hydrogenation step (A1) or (B1) is performed in the presence of a metal catalyst, a catalyst modifier, wherein the catalyst modifier is selected from 3,6-dithia-1,8-octadiole, $FeBr_3$, $FeCl_3$, $Fe(OAc)_2$, KBr, $MgBr_2$, MgO, NaBr, $NH_4VO_3$, chinoline, n-tetramethylammonium bromide, n-tetraethylammonium bromide, n-tetrabutylammoniumbromide, tetrahydrothiophene, thioethanole, V(V) oxide, V(IV) oxide and $ZnBr_2$, and the acid $H_2SO_4$ in the solvent methanol, wherein the amount of the catalyst modifier is in the range from about 0.01 equivalents to about 0.2 equivalents with respect to the amount of cyanopyridyl derivative according to formula (II).

Very particular preferably the hydrogenation step (A1) or (B1) is performed in the presence of a metal catalyst, a catalyst modifier, wherein the catalyst modifier is n-tetrabutylammoniumbromide, and the acid $H_2SO_4$ in the solvent methanol, wherein the amount of the catalyst modifier is in the range from about 0.01 equivalents to about 0.2 equivalents with respect to the amount of cyanopyridyl derivative according to formula (II).

Particular preferably the hydrogenation step (A1) or (B1) is performed in the presence of a metal catalyst, wherein the metal catalyst is selected from Pd/C, Pd/$Al_2O_3$, Pd(OH)$_2$/C, Palladium oxide/C, mixed Palladium oxide-hydroxide/C, Palladium oxide/$Al_2O_3$, mixed Palladium oxide-hydroxide/$Al_2O_3$, Palladium oxide/$SiO_2$, mixed Palladium oxide-hydroxide/$SiO_2$ and Pd/$SiO_2$ having a metal loading in the range of 5 to 20%, a catalyst modifier, and the acid $H_2SO_4$ in the solvent methanol, wherein the amount of the catalyst modifier is in the range from about 0.01 equivalents to about 0.2 equivalents with respect to the amount of cyanopyridyl derivative according to formula (II).

Very particular preferably the hydrogenation step (A1) or (B1) is performed in the presence of a metal catalyst, wherein the metal catalyst is selected from Pd/C, Pd/Al$_2$O$_3$, Pd(OH)$_2$/C, Palladium oxide/C, and mixed Palladium oxide-hydroxide/C having a metal loading in the range of 5 to 20%, a catalyst modifier, and the acid H$_2$SO$_4$ in the solvent methanol, wherein the amount of the catalyst modifier is in the range from about 0.01 equivalents to about 0.2 equivalents with respect to the amount of cyanopyridyl derivative according to formula (II).

Even more preferably the hydrogenation step (A1) or (B1) is performed in the presence of a metal catalyst, wherein the metal catalyst is selected from Pd/C, Pd/Al$_2$O$_3$, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/SiO$_2$ having a metal loading in the range of 5 to 20%, a catalyst modifier, wherein the catalyst modifier is selected from 3,6-dithia-1,8-octadiole, FeBr$_3$, FeCl$_3$, Fe(OAc)$_2$, KBr, MgBr$_2$, MgO, NaBr, NH$_4$VO$_3$, chinoline, n-tetramethylammonium bromide, n-tetraethylammonium bromide, n-tetrabutylammoniumbromide, tetrahydrothiophene, thioethanole, V(V) oxide, V(IV) oxide or ZnBr$_2$, and the acid H$_2$SO$_4$ in the solvent methanol, wherein the amount of the catalyst modifier is in the range from about 0.01 equivalents to about 0.2 equivalents with respect to the amount of cyanopyridyl derivative according to formula (II).

Particular preferably the hydrogenation step (A1) or (B1) is performed in the presence of a metal catalyst, wherein the metal catalyst is selected from Pd/C, Pd/Al$_2$O$_3$, Pd(OH)$_2$/C, Palladium oxide/C, mixed Palladium oxide-hydroxide/C having a metal loading in the range of 5 to 20%, a catalyst modifier, wherein the catalyst modifier is selected from 3,6-dithia-1,8-octadiole, FeBr$_3$, FeCl$_3$, Fe(OAc)$_2$, KBr, MgBr$_2$, MgO, NaBr, NH$_4$VO$_3$, chinoline, n-tetramethylammonium bromide, n-tetraethylammonium bromide, n-tetrabutylammoniumbromide, tetrahydrothiophene, thioethanole, V(V) oxide, V(IV) oxide or ZnBr$_2$, and the acid H$_2$SO$_4$ in the solvent methanol, wherein the amount of the catalyst modifier is in the range from about 0.01 equivalents to about 0.2 equivalents with respect to the amount of cyanopyridyl derivative according to formula (II).

Particular preferably the hydrogenation step (A1) or (B1) is performed in the presence of a metal catalyst, wherein the metal catalyst is selected from Pd/C, Pd/Al$_2$O$_3$, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/SiO$_2$ having a metal loading in the range of 5 to 20%, a catalyst modifier, wherein the catalyst modifier is selected from NaBr, n-tetramethylammonium bromide, n-tetraethylammonium bromide, n-tetrabutylammoniumbromide or ZnBr$_2$, and the acid H$_2$SO$_4$ in the solvent methanol, wherein the amount of the catalyst modifier is in the range from about 0.01 equivalents to about 0.2 equivalents with respect to the amount of cyanopyridyl derivative according to formula (II).

Very particular preferably the hydrogenation step (A1) or (B1) is performed in the presence of a metal catalyst, wherein the metal catalyst is selected from Pd/C, Pd/Al$_2$O$_3$, Pd(OH)$_2$/C, Palladium oxide/C, mixed Palladium oxide-hydroxide/C having a metal loading in the range of 5 to 20%, a catalyst modifier, wherein the catalyst modifier is selected from NaBr, n-tetramethylammonium bromide, n-tetraethylammonium bromide, n-tetrabutylammoniumbromide or ZnBr$_2$, and the acid H$_2$SO$_4$ in the solvent methanol, wherein the amount of the catalyst modifier is in the range from about 0.01 equivalents to about 0.2 equivalents with respect to the amount of cyanopyridyl derivative according to formula (II).

Most preferably the hydrogenation step (A1) or (B1) is performed in the presence of a metal catalyst, wherein the metal catalyst is Pd(OH)$_2$/C having a metal loading of 20%, a catalyst modifier, wherein the catalyst modifier is n-tetrabutylammoniumbromide, and the acid H$_2$SO$_4$ in the solvent methanol, wherein the amount of the catalyst modifier is in the range from about 0.01 equivalents to about 0.2 equivalents with respect to the amount of cyanopyridyl derivative according to formula (II).

Most preferably process (A) comprises the steps (A1) and (A1a) as defined above.

More preferably the acylation step (B2) is performed in a suitable solvent wherein the solvent is selected from water, methanol, ethanol, iso-propanol, propanol, n-butanol and iso-butanol in the presence of a suitable base wherein the base is selected from NaOH, KOH and Ca(OH)$_2$.

Particular preferably the acylation step (B2) is performed in a suitable solvent wherein the solvent is selected from water and methanol in the presence of a suitable base wherein the base is selected from NaOH and KOH.

Most preferably the acylation step (B2) is performed in a suitable solvent, wherein the solvent is methanol in the presence of a suitable base wherein the base is NaOH.

Preferably process (B) comprises an additional step (B1a) after step (B1), wherein a suitable base is added to the reaction mixture comprising the 2-methylaminopyridine derivative of formula (III) after filtering off the catalyst to adjust the pH value.

More preferably process (B) comprises an additional step (B1a) after step (B1), wherein a suitable base which is selected from NaOH, KOH and Ca(OH)$_2$, is added to the reaction mixture comprising the 2-methylaminopyridine derivative of formula (III) after filtering off the catalyst to adjust the pH to a value of pH 6 to 9.

Preferably process (B) comprises an additional step (B3) after step (B2), wherein a suitable acid is added to the reaction mixture comprising the pyridylmethylbenzamides of formula (I) to adjust the pH value.

More preferably process (B) comprises an additional step (B3) after step (B2), wherein a suitable acid which is selected from as hydrochloric acid (HCl), sulfuric acid (H$_2$SO$_4$) and phosphoric acid (H$_3$PO$_4$) is added to the reaction mixture comprising the pyridylmethylbenzamides of formula (I) to adjust the pH to a value of 2 to 4.

Preferably process (B) comprises an additional step (B4) after step (B3), wherein the reaction mixture comprising the pyridylmethylbenzamides of formula (I) is filtered and the residue washed with a suitable solvent which is selected from hexane, cyclohexane, methylcyclohexane, benzene, toluene and xylene.

Most preferably process (B) comprises the steps (B1), (B1a), (B2), (B3) and (B4) as defined above.

All of the aforementioned preferred, more preferred, even more preferred, particular preferably, very particular preferably and most preferably embodiments with respect to derivatives of formulas (I), (II), (III) and (IV) apply for derivatives of formulas (Ia), (IIa), (IIIa) and (IVa) respectively.

The process according to the invention is suitable for large scale production. The overall yield is higher and less dehalogenated side products which create problems during work-up procedures are obtained. Surprisingly it has been found that by following the process according to the invention hydrogenation and acylation steps do not have to be worked up separately. This procedure avoids issues with isolation of 2-methylaminopyridine derivatives of formula (III) and with the handling of the isolated material. Thus, the process according to the invention provides access to pyridylbenzamide derivatives of formula (I), particular preferably to Fluopicolide of formula (Ia), in a more economic and environmentally friendly way.

Methods and Abreviations

Methods

Method 1 (HPLC): Instrument: Agilent 1100; column: Zorbax Eclipse XDB-C18 1.8μ, 50 mm×4.6 mm; eluent A: 1 L water+1 mL phosphoric acid, eluent B: acetonitrile; gradient: 0.0 min 90% A→4.25 min 5% A→6.0 min 5% A→6.01 min 90% A; column temperature: 55° C.; flow rate: 2.0 mL/min; UV detection: 210 nm.

Abbreviations

HPLC high pressure liquid chromatography
w/w weight/weight

EXAMPLES

The examples shown below further illustrate the invention without limiting it.

Examples regarding Process (A):

Example 1

Hydrogenation with Different Catalyst, Different Modifiers and Sulfuric Acid

An autoclave can be charged with a solution of 3-chloro-2-cyano-5-trifluoromethylpyridine [Py-CN], a modifier at an amount between 0.0001 to 0.1 equivalents related to the amount of [Py-CN] and an acid in a solvent, followed by the addition of the catalyst. The catalyst, modifier, acid, and solvent can be chosen from the tables 1a, 1b, 1c and 1d below.

The contents can then be stirred at an elevated hydrogen pressure of more than 5 bar at 20° C. for 4 h-hydrogen uptake ceased after 3 hours and stirring can be continued for another hour. The reaction mixture can be removed by filtration from the autoclave. In case of recyclization the above described procedure is repeated under the same conditions as described above with the exception that the amount of the modifier can be reduced up to 0.02 equivalents. The removed reaction mixture can be analyzed by HPLC to quantify the content of amine.

TABLE 1a

Catalysts
The catalysts are commercially available catalysts from companies
(e.g. BASF, Acros, Evonik).

| Ref. | Catalyst |
| --- | --- |
| c1 | Pd |
| c2 | Pd/C |
| c3 | Pd(OH)$_2$/C |
| c4 | Pd/Al$_2$O$_3$ |
| c5 | Palladium oxide/C |
| c6 | mixed Palladium oxide-hydroxide/C |
| c7 | Palladium oxide/Al$_2$O$_3$ |
| c8 | mixed Palladium oxide-hydroxide/Al$_2$O$_3$ |
| c9 | Palladium/SiO$_2$ |
| c10 | Palladium oxide/SiO$_2$ |
| c11 | mixed Palladium oxide-hydroxide/SiO$_2$ |
| c12 | Pd/CaCO$_3$ |
| c13 | Pd/C-diphenylsulfide |
| c14 | Pd/BaSO$_4$ |
| c15 | Pd(II)acetate-Polymethylhydrosiloxane |

TABLE 1a-continued

Catalysts
The catalysts are commercially available catalysts from companies
(e.g. BASF, Acros, Evonik).

| Ref. | Catalyst |
| --- | --- |
| c16 | Pd (Fe)/C |
| c17 | Pd/C 5% sulfur |
| c18 | 5% Pd/0.5% V |
| c19 | Pd/Pt |

TABLE 1b

| Ref. | Modifier |
| --- | --- |
| m1 | Thiophene |
| m2 | Tetrahydrothiophene |
| m3 | 2-Mercaptophenol |
| m4 | Cysteine |
| m5 | 3,6-Dithia 1,8 octadiol |
| m6 | 2,2'-Thiobisethanol |
| m7 | Diphenyl sulfide |
| m8 | Thiophenol |
| m9 | Thioanisole |
| m10 | Sulfolane |
| m11 | Thiourea |
| m12 | Na$_2$S$_2$O$_3$—xH$_2$O |
| m13 | Na$_2$S |
| m14 | Chinoline |
| m15 | PPh$_3$ |
| m16 | Mo(CO)$_6$ |
| m17 | V(V) oxide |
| m18 | V(IV) oxide |
| m19 | V(III) sulfide |
| m20 | NH$_4$VO$_3$ |
| m21 | ZnBr$_2$ |
| m22 | ZnCl$_2$ |
| m23 | MgBr$_2$ |
| m24 | MgO |
| m25 | FeCl$_2$ |
| m26 | FeCl$_3$ |
| m27 | Fe(OAc)$_2$) |
| m28 | n-Tetramethylammonium iodide |
| m29 | n-Tetraethylammonium iodide |
| m30 | n-Tetrabutylammonium iodide |
| m31 | n-Tetramethylammonium bromide (TMAB) |
| m32 | n-Tetraethylammonium bromide |
| m33 | n-Tetrabutylammoniumbromide (TBAB) |
| m34 | n-Tetramethylammonium chloride |
| m35 | n-Tetraethylammonium chloride |
| m36 | n-Tetrabutylammoniumchloride |
| m37 | NaCl |
| m38 | NaBr |
| m39 | NaI |
| m40 | KCl |
| m41 | KBr |
| m42 | KI |
| m43 | LiBr |
| m44 | MgBr$_2$ |
| m45 | AlCl$_3$ |
| m46 | CeCl$_3$ |
| m47 | CuCl |
| m48 | CuBr |
| m49 | CuI |
| m50 | CuBr$_2$ |
| m51 | BaSO$_4$ |

TABLE 1c

| Acid | |
|---|---|
| Ref. | Acid |
| a1 | Sulfuric acid |
| a2 | Phosphoric acid |
| a3 | Methanesulfonic acid |

TABLE 1d

| Solvent | |
|---|---|
| Ref. | Solvent |
| s1 | Methanol |
| s2 | Ethanol |
| s3 | isopropanol |
| s4 | t-butanol |
| s5 | tetrahydrofuran |
| s6 | methyltetrahydrofuran |

From the tables 1a, 1b, 1c and 1d any combination of catalyst, modifier, acid and solvent can be selected.

Surprisingly it has been found that the amount of the dehalogenated side-products can be reduced to equal or less than 1% of the end product with the above described processes.

Example 1A 2,6-Dichloro-N-{[3-chloro-5-(trifluoromethyl)pyridin-2-yl]methyl}benzamide [Fluopicolide]

Step a)

1-[3-Chloro-5-(trifluoromethyl)pyridin-2-yl]methanamine (PyMA)

To a solution of 144.59 g (700 mmole, 100.0% purity) 3-Chloro-5-(trifluoromethyl)pyridine-2-carbonitrile (PyCN) and 22.79 g (10 mol %, >99% purity) Tetra-n-butyl ammonium bromide (TBAB) in 460 g Methanol (>99% purity) at 20° C. were added slowly 85.82 g (840 mmole, 96%) sulfuric acid. The internal temperature of the reaction mixture was kept below 20° C. Once the addition is complete the reaction mixture was transferred into an autoclave and 15.96 g Palladium hydroxide on carbon (Noblyst P1071 20% Pd) were added. The autoclave is purged twice with nitrogen. The mixture is stirred for 15 minutes. The stirrer is turned off. The autoclave is purged once with hydrogen and pressurized to 20 bar hydrogen pressure. The contents are then stirred at 20° C. for 1 to 2 hours—hydrogen uptake ceased after about 1 hour (at first run) and stirring was continued for another 15 minutes. After depressurization of the autoclave to atmospheric pressure, the catalyst is removed by filtration and washed with methanol to give 1-[3-Chloro-5-(trifluoromethyl)pyridin-2-yl]methanamine (PyMA) as a methanolic solution (20%, 703.5 g, 674.7 mmole, 96.4% yield).

HPLC (Method 1): $R_t$=0.786 min.

Step b)—Alternative 1

2,6-Dichloro-N-{[3-chloro-5-(trifluoromethyl)pyridin-2-yl]methyl}benzamide [Fluopicolide]

To a solution of 1120.4 g (1159 mmol, 21.8 wt % purity) 1-[3-Chloro-5-(trifluoromethyl)pyridin-2-yl]methanamine-hydrogensulfate in Methanol at 20° C. 115.3 g of an aqueous sodium hydroxide solution (32% w/w) were added slowly until pH 7. The internal temperature of the mixture was kept below 20° C.

To the reaction mixture 243.1 g (1159 mmol) 2,6-dichlorobenzoyl chloride and 225.6 g aqueous sodium hydroxide solution (32% w/w) were added simultaneously at 20° C. within approx. one hour. The suspension was allowed to proceed for another hour followed by addition of 1.6 g (20% w/w) hydrochloric acid until the pH is adjusted to 3. The suspension was filtered at 20° C. by suction filtration and the filter cake was washed first with 843 g water at 70° C. and once again with 843 g water at 70° C. The residue was subsequently washed with 193 g methyl cyclohexane at 40° C. and once again with 193 g methyl cyclohexane at 40° C. The solid was transferred to a dryer and dried at 40° C. and 20 mbar to obtain 441.4 g (1134.6 mmol, 97.7% yield) of the title compound in 98.6% purity.

HPLC (Method 1): $R_t$=3.28 min.

Step b)—Alternative 2

2,6-Dichloro-N-{[3-chloro-5-(trifluoromethyl)pyridin-2-yl]methyl}benzamide [Fluopicolide]

A reactor was charged with 124.77 g 1-[3-Chloro-5-(trifluoromethyl)pyridin-2-yl]methanamine-Hydrogenchloride (500 mmol, 99%) and 500 g water. The solution was cooled down to about 20° C. followed by the addition of an aqueous solution of sodium hydroxide (32% w/w) to adjust the pH to 7.5. To the reaction mixture 105.88 g (505 mmol) 2,6-dichlorobenzoyl chloride and about 123 g aqueous sodium hydroxide solution (32% w/w) were added simultaneously at 20° C. within approx. 1.5 hour at pH 6 to 8. The suspension was allowed to proceed for another hour at 20° C. at pH 6-8 followed by addition of 200 g water. The suspension was filtered at 20° C. by suction filtration and the filter cake was washed twice with 150 g of a methanol-water-mixture (2:1). The solid was transferred to a dryer and dried at 40° C. and 20 mbar to obtain 189.5 g (95.7% yield) of the title compound in 96.9% purity.

HPLC (Method 1): $R_t$=3.28 min.

The invention claimed is:

1. A process for preparation of one or more substituted pyridylmethylbenzamides of formula (I)

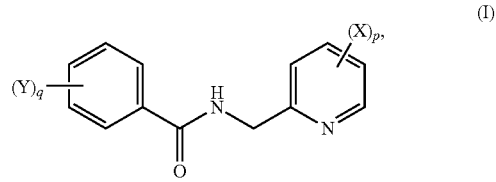

wherein p is an integer equal to 1, 2, 3 or 4, q is an integer equal to 1, 2, 3 or 4, each substituent X is, independently of the others, hydrogen, halogen, $C_1$-$C_4$ alkyl or $C_1$-$C_4$ haloalkyl with the proviso that the at least one X is halogen, Y is halogen, comprising in a step (B1) hydrogenating a substituted cyanopyridyl derivative according to formula (II)

wherein p and X are defined as above, in the presence of a metal catalyst, a catalyst modifier and an acid, wherein an amount of the catalyst modifier is in a range from about 0.0000001 equivalents to about 10 equivalents with respect to the amount of cyanopyridyl derivative according to formula (II), to give a compound of formula (III) or corresponding salts thereof

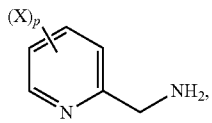
(III)

wherein p and X are defined as above,
and further comprising in a step (B2) reacting the compound of formula (III) or one or more corresponding salts thereof,

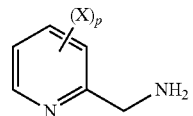
(III)

wherein p is an integer equal to 1, 2, 3 or 4;
each substituent X is, independent of the others, halogen, $C_1$-$C_4$ alkyl or $C_1$-$C_4$ haloalkyl;
in a suitable solvent in the presence of a suitable base with a compound of formula (IV)

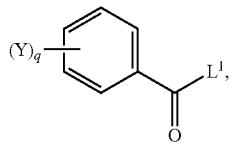
(IV)

wherein
q is an integer equal to 1, 2, 3 or 4,
Y is halogen and
$L^1$ is a leaving group,
to give one or more substituted pyridylmethylbenzamids of formula (I);
wherein an amount of dehalogenated side-products is less than or equal to 1% of the one or more substituted pyridylmethylbenzamides of formula (I) produced by the process; and
wherein the catalyst modifier is selected from the group consisting of n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, and n-tetrabutylammoniumchloride.

2. The process according to claim 1,
wherein p is 1 or 2;
each substituent X is, independent of the others, fluorine, chlorine, difluoromethyl, trifluoromethyl, dichloromethyl, or trichloromethyl; and
the 2-pyridyl moiety is substituted by X in 3- and/or in 5-position.

3. The process according to claim 1,
wherein the compound according to formula (III) is 2-aminomethyl-3-chloro-5-trifluoromethylpyridine.

4. The process according to claim 1, wherein the acid is selected from group consisting of acetic acid ($CH_3CO_2H$), methanesulfonic acid and $H_2SO_4$.

5. The process according to claim 1, wherein the concentration of the catalyst modifier is in the range from about 0.01 equivalents to about 0.2 equivalents with respect to the amount of cyanopyridyl derivative according to formula (II).

6. The process according to claim 1, wherein the process is repeated under the same conditions with the exception that the catalyst is recycled and the modifier concentration is in the range from about 0.0000001 equivalents to up to 0.05 equivalents.

7. The process according to claim 1, wherein the substituted pyridylmethylbenzamides of formula (I) comprises a compound of formula (Ia),

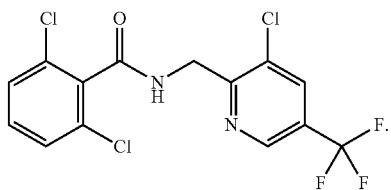 [SMILES: O=C(NCc1ncc(C(F)(F)F)cc1Cl)c1c(Cl)cccc1Cl]

8. The process according to claim 1, wherein the catalyst modifier is in the range from about 0.001 equivalents to about 2 equivalents with respect to the amount of cyanopyridyl derivative according to formula (II).

9. The process according to claim 1, wherein the catalyst modifier is in the range from about 0.01 equivalents to about 0.2 equivalents with respect to the amount of cyanopyridyl derivative according to formula (II).

10. The process according to claim 1, wherein the catalyst modifier is selected from the group consisting of n-tetramethylammonium bromide, n-tetraethylammonium bromide, and n-tetrabutylammoniumbromide.

11. The process according to claim 1, wherein the metal catalyst is selected from the group consisting of Pd/C, Pd/$Al_2O_3$, Pd(OH)$_2$/C, Palladium oxide/C, mixed Palladium oxide-hydroxide/C, Palladium oxide/$Al_2O_3$, mixed Palladium oxide-hydroxide/$Al_2O_3$, Palladium oxide/$SiO_2$, mixed Palladium oxide-hydroxide/$SiO_2$ and Pd/$SiO_2$ having a metal loading in a range of 5 to 20%.

12. The process according to claim 1, wherein the solvent is selected from the group consisting of methanol, ethanol, isopropanol, t-butanol, tetrahydrofuran, and methyltetrahydrofuran.

13. The process according to claim 1, further comprising, after (B1),
(B1a) removing a solvent of a reaction solution comprising the 2-methylaminopyridine derivative according to formula (III).

14. The process according to claim 13, further comprising, after (B1a),
(B1b) adding a base to remaining residue of (B1a).

15. The process according to claim 14, further comprising, after (B1b),
(B1c) separating the organic phase from the water phase.

16. The process according to claim 15, further comprising, after (B1c),
(B1d) isolating a precipitated product according to formula (III) from a reaction suspension comprising the 2-methylaminopyridine derivative according to formula (III) or corresponding salt thereof.

17. The process according to claim 14, further comprising before (B1b), at the same time as (B1b), or thereafter, adding an organic solvent to remaining residue of (B1a).

18. The process according to claim 15, wherein (B1c) further comprises adding an acid to the organic phase.

* * * * *